(12) United States Patent
Mourich et al.

US007989608B2

(10) Patent No.: US 7,989,608 B2
(45) Date of Patent: Aug. 2, 2011

(54) IMMUNOMODULATORY AGENTS AND METHODS OF USE

(75) Inventors: Dan V. Mourich, Albany, OR (US); Patrick L. Iversen, Corvallis, OR (US)

(73) Assignee: AVI BioPharma Inc., Corvallis, OR (US)

( * ) Notice: Subject to any disclaimer, the term of this patent is extended or adjusted under 35 U.S.C. 154(b) by 0 days.

(21) Appl. No.: 12/344,143

(22) Filed: Dec. 24, 2008

(65) Prior Publication Data

US 2009/0246221 A1 Oct. 1, 2009

Related U.S. Application Data

(60) Provisional application No. 61/009,464, filed on Dec. 28, 2007.

(51) Int. Cl.
C07H 21/04 (2006.01)
C12N 15/11 (2006.01)
(52) U.S. Cl. ...................... 536/23.1; 514/44 A
(58) Field of Classification Search ............... None
See application file for complete search history.

(56) References Cited

U.S. PATENT DOCUMENTS

| | | | |
|---|---|---|---|
| 5,034,506 A | 7/1991 | Summerton et al. | 528/391 |
| 5,142,047 A | 8/1992 | Summerton et al. | 544/118 |
| 5,166,315 A | 11/1992 | Summerton et al. | 528/406 |
| 5,185,444 A | 2/1993 | Summerton et al. | 544/81 |
| 5,217,866 A | 6/1993 | Summerton et al. | 435/6 |
| 5,506,337 A | 4/1996 | Summerton et al. | 528/391 |
| 5,521,063 A | 5/1996 | Summerton et al. | 435/6 |
| 5,698,685 A | 12/1997 | Summerton et al. | 536/24.3 |
| 5,892,023 A | 4/1999 | Pirotzky et al. | 536/24.5 |
| 6,210,892 B1 | 4/2001 | Bennett et al. | 435/6 |
| 6,784,291 B2 | 8/2004 | Iversen et al. | 536/24.5 |
| 7,468,418 B2 | 12/2008 | Iversen et al. | 530/300 |
| 7,807,816 B2 | 10/2010 | Wilton et al. | 536/24.5 |
| 2002/0049173 A1 | 4/2002 | Bennett et al. | 514/44 |
| 2003/0224353 A1 | 12/2003 | Stein et al. | 435/5 |
| 2006/0276425 A1 | 12/2006 | Mourich et al. | 514/44 |
| 2006/0287268 A1 | 12/2006 | Iversen et al. | 514/44 |
| 2007/0111962 A1 | 5/2007 | Mourich et al. | |
| 2007/0122821 A1 | 5/2007 | Iversen et al. | 435/6 |
| 2007/0155685 A1 | 7/2007 | Schlingensiepen | |
| 2009/0082547 A1 | 3/2009 | Iversen et al. | 530/322 |
| 2009/0088562 A1 | 4/2009 | Weller et al. | 536/24.5 |
| 2009/0099066 A1 | 4/2009 | Moulton et al. | 514/7 |
| 2009/0110689 A1 | 4/2009 | Mourich et al. | 424/184.1 |
| 2010/0130591 A1 | 5/2010 | Sazani et al. | 514/44 A |
| 2010/0184670 A1 | 7/2010 | Mourich et al. | 514/12 |

FOREIGN PATENT DOCUMENTS

| WO | WO 01/49775 | 7/2001 |
|---|---|---|
| WO | WO 01/72765 | 10/2001 |
| WO | WO 01/83740 | 11/2001 |
| WO | WO 2006/000057 | 1/2006 |
| WO | WO 2006/086667 | 8/2006 |
| WO | WO 2006/108241 A1 | 10/2006 |
| WO | WO 2010/048586 | 4/2010 |
| WO | WO 2010/080554 | 7/2010 |

OTHER PUBLICATIONS

Gewirtz et al (PNSA USA vol. 93, pp. 3161-3163, 1996).*
The International Search Report and Written Opinion for PCT application PCT/US2008/088339, search report dated Jun. 4, 2009, 13 pages (2009).
Akdis, C. A. and Blaser, K., "Mechanisms of interleukin-10-mediated immune suppression." *Immunology*, 103(2):131-6 (2001).
Banchereau, J. and A. K. Palucka, "Dendritic cells as therapeutic vaccines against cancer." *Nature Reviews Immunology*, 5(4):296-306 (2005).
Barcova, M. et al., "gp41 envelope protein of human immunodeficiency virus induces interleukin (IL)-10 in monocytes, but not in B, T, or NK cells, leading to reduced IL-2 and interferon-gamma production." *Journal of Infectious Diseases*, 177(4):905-13 (1998).
Biswas, P. S. et al., "Pathogen-specific CD8 T cell responses are directly inhibited by IL-10." *The Journal of Immunology*, 179(7):4520-8 (2007).
Boland, A. and Cornelis, C.R., "Role of YopP in suppression of tumor necrosis factor alpha release by macrophages during Yersinia infection.", *Infection and Immunity*, 66(5):1878-84 (1998).
Boussiotis, V. et al., "IL-10-producing T cells suppress immune responses in anergic tuberculosis patients", *The Journal of Clinical Investigation*, 105(9):1317-25 (2000).
Brady, M. T., A. J. MacDonald, et al. (2003). "Hepatitis C virus non-structural protein 4 suppresses Th1 responses by stimulating IL-10 production from monocytes." *European Journal of Immunology*, 33(12):3448-57 (2003).
Bray, M. et al.,"A mouse model for evaluation of prophylaxis and therapy of Ebola hemorrhagic fever", *The Journal of Infectious Diseases*, 178(3):651-61 (1998).
Brooks, D. G. et al., "Interleukin-10 determines viral clearance or persistence in vivo", *Nature Medicine*, 12(11):1301-9 (2006).
Cappuccio, A. et al., "Determination of the optimal therapeutic protocols in cancer immunotherapy", *Mathematical Biosciences*, 209(1):1-13 (2007).
Cornelis, G. R. and G. Denecker. "Yersinia lead SUMO attack", *Nature. Medicine*, 7(1):21-3 (2001).
Crooke, S. T. Antisense Drug Technology: Principles, Strategies, and Applications. New York, Marcel Dekker, S. Crooke Ed Springer pp. 1-50 (1999).
Dercamp, C. et al., "Distinct and overlapping roles of interleukin-10 and CD25+ regulatory T cells in the inhibition of antitumor CD8 T-cell responses", *Cancer Research*, 65(18):8479-86 (2005).
Ejrnaes, M. et al., "Resolution of a chronic viral infection after interleukin-10 receptor blockade", *The Journal of Experimental. Medicine*, 203(11):2461-2472 (2006).

(Continued)

*Primary Examiner* — Albert Navarro
(74) *Attorney, Agent, or Firm* — Seed IP Law Group PLLC

(57) ABSTRACT

An antisense oligonucleotide compound, composition, vaccine and methods for treating a variety of conditions characterized by up-regulation of IL-10 in a mammalian subject are disclosed. The compound (i) is composed of morpholino subunits and phosphorus-containing intersubunit linkages joining a morpholino nitrogen of one subunit to a 5' exocyclic carbon of an adjacent subunit, (ii) is capable of uptake by monocytes, lymphocytes, and dendritic cells in a mammalian subject, (iii) contains between 10-40 nucleotide bases, and (iv) has a base sequence effective to hybridize to at least 12 contiguous bases of a target sequence contained in an exon-2 or exon-4 slice site region of human IL-10 pre-mRNA.

22 Claims, 11 Drawing Sheets

OTHER PUBLICATIONS

Encke, J. et al., "Prophylactic and therapeutic vaccination with dendritic cells against hepatitis C virus infection", *Clinical and Experimental Immunology*, 142(2):362-9 (2005).

Fleming S. B. et al., "A homolog of interleukin-10 is encoded by the poxvirus orf virus", *Jornal of Virology*, 71(6):4857-61 (1997).

Gong, J. H. et al., "Interleukin-10 downregulates Mycobacterium tuberculosis-induced Th1 responses and CTLA-4 expression", *Infection and Immunity*, 64(3):913-8 (1996).

Guerrero-Plata, A. et al.,"Differential response of dendritic cells to human metapneumovirus and respiratory syncytial virus", *Am J Respir Cell Mol Biol.*, 34(3):320-9 (2006).

Igietseme, J. U. et al., "Suppression of Endogenous IL-10 Gene Expression in Dendritic Cells Enhances Antigen Presentation for Specific Th1 Induction: Potential for Cellular Vaccine Development", *The Journal of Immunology*, 164(8):4212-4219 (2000).

Jacobs, M. et al.,"Increased resistance to mycobacterial infection in the absence of interleukin-10", *Immunology*, 100(4): 494-501 (2000).

Kornbluth, R. S. and Stone, G.W., "Immunostimulatory combinations: designing the next generation of vaccine adjuvants", *Journal of Leukocyte Biology*, 80(5):1084-102 (2006).

Koutsonikolis, A., S. Haraguchi, et al. (1997). "HIV-1 recombinant gp41 induces IL-10 expression and production in peripheral blood monocytes but not in T-lymphocytes." *Immunology Letters*, 55(2):109-13 (1997).

Liu, G. et al., "Small interference RNA modulation of IL-10 in human monocyte-derived dendritic cells enhances the Th1 response." *Eur J Immunol.*, 34(6):1680-7 (2004).

Marin-Serrano, E. et al., "Modulation of the anti-inflammatory interleukin 10 and of proapoptotic IL-18 in patients with chronic hepatitis C treated with interferon alpha and ribavirin." *Journal of Viral Hepatitis*, 13(4):230-4 (2006).

Marshall, N. B. et al., "Arginine-rich cell-penetrating peptides facilitate delivery of antisense oligomers into murine leukocytes and alter pre-mRNA splicing." *Journal of Immunological Methods*, 325(1-2):114-126 (2007).

Miyada, C. G. and Wallace, R.B., "Oligonucleotide hybridization techniques." *Methods in Enzymology*, 154:94-107 (1987).

Mocellin, S. et al., "Kinetics of cytokine expression in melanoma metastases classifies immune responsiveness." *Int J Cancer*, 93(2):236-42 (2001).

Moore, K. W. et al., "Interleukin-10 and the interleukin-10 receptor." *Annu Rev Immunol.*, 19:683-765 (2001).

Murray, P. J. and Young, R.A., "Increased antimycobacterial immunity in interleukin-10-deficient mice." *Infection and Immunity*, 67(6):3087-95 (1999).

Nielsen, E., "RNA targeting using peptide nucleic acid." *Handb Exp Pharmacol.*, 173:395-403 (2006).

Nigou, J. et al., "Mannosylated lipoarabinomannans inhibit IL-12 production by human dendritic cells: evidence for a negative signal delivered through the mannose receptor." *The Journal of Immunology*, 166(12):7477-85 (2001).

Oh, J. H. et al., "Polymorphisms of interleukin-10 and tumour necrosis factor-alpha genes are associated with newly diagnosed and recurrent pulmonary tuberculosis", *Respirology*, 12(4):594-8 (2007).

Oral, H. B. et al., "Interleukin-10 (IL-10) gene polymorphism as a potential host susceptibility factor in tuberculosis", *Cytokine*, 35(3-4):143-7 (2006).

Orsilles, M. A. et al., "IL-2 and IL-10 serum levels in HIV-1-infected patients with or without active antiretroviral therapy" *Apmis* 114(1):55-60 (2006).

Rigopoulou, E. I.et al., "Blocking of interleukin-10 receptor—a novel approach to stimulate T-helper cell type 1 responses to hepatitis C virus", *Clinical Immunology*, 117(1):57-64 (2005).

Romani, N. et al. "Proliferating dendritic cell progenitors in human blood." *The Journal of Experimental Medicine*,180(1):83-93 (1994).

Schols, D. and De Clercq, E., "Human immunodeficiency virus type 1 gp120 induces anergy in human peripheral blood lymphocytes by inducing interleukin-10 production", *Journal of Virology*, 70(8):4953-60 (1996).

Stockl, J. et al., "Human major group rhinoviruses downmodulate the accessory function of monocytes by inducing IL-10", *The Journal of Clinical Investigation*, 104(7):957-65 (1999).

Summerton, J. and Weller, D., "Morpholino antisense oligomers: design, preparation, and properties", *Antisense Nucleic Acid Drug Dev.*, 7(3):187-95 (1997).

Suzuki, T. et al., "Viral interleukin 10 (IL-10), the human herpes virus 4 cellular IL-10 homologue, induces local anergy to allogeneic and syngeneic tumors." *The Journal of Experimental Medicine*, 182(2) : 477-486 (1995).

Taoufik, Y. et al., "Human immunodeficiency virus gp120 inhibits interleukin-12 secretion by human monocytes: an indirect interleukin-10-mediated effect." *Blood*, 89(8):2842-8 (1997).

Tufariello, J. M. et al.,"Adenovirus E3 14.7-kilodalton protein, an antagonist of tumor necrosis factor cytolysis, increases the virulence of vaccinia virus in severe combined immunodeficient mice.", *Proc Natl Acad Sci U S A*, 91(23):10987-91 (1994).

Tufariello, J., S. et al.,"The adenovirus E3 14.7-kilodalton protein which inhibits cytolysis by tumor necrosis factor increases the virulence of vaccinia virus in a murine pneumonia model", *Journal of Virology*, 68(1):453-62 (1994).

Van Gulck, E. R. A. et al., "Efficient stimulation of HIV-1-specific T cells using dendritic cells electroporated with mRNA encoding autologous HIV-1 Gag and Env proteins", *Blood*,107(5):1818-1827 (2006).

Vicari, A. P.et al., "Reversal of tumor-induced dendritic cell paralysis by CpG immunostimulatory oligonucleotide and anti-interleukin 10 receptor antibody." *J Exp Med.*, 196(4):541-9 (2002).

Vockerodt, M.et al.,"The Epstein-Barr virus latent membrane protein 1 induces interleukin-10 in Burkitt's lymphoma cells but not in Hodgkin's cells involving the p38/SAPK2 pathway." *Virology*, 280(2):183-98 (2001).

Yu, D. H. et al., "A combined DNA vaccine enhances protective immunity against Mycobacterium tuberculosis and Brucella abortus in the presence of an IL-12 expression vector." *Vaccine*, 25(37-38):6744-54 (2007).

Agrawal et al., "Oligodeoxynucleoside phosphoramidates and phosphorothioates as inhibitors of human immunodeficiency virus," *Proc. Natl. Acad. Sci. USA* 85:7079-7083, 1988.

Amantana et al., "Pharmacokinetics and biodistribution of phosphorodiamidate morpholino antisense and oligomers," *Current Opinion in Pharmacology* 5:550-555, 2005.

Futaki et al., "Arginine-rich peptides and their internalization mechanisms," *Biochem. Soc. Trans.* 35(Pt. 4):784-787, 2007. (Abstract).

International Search Report for International Application No. PCT/US2000/008174, mailed Jul. 25, 2000, 2 pages.

International Search Report for International Application No. PCT/US2001/014410, mailed Mar. 6, 2002, 5 pages.

International Search Report for International Application No. PCT/US2009/068599, mailed May 21, 2010, 3 pages.

Moulton et al., "Compound and Method for Treating Myotonic Dystrophy," U.S. Appl. No. 12/493,140, filed Jun. 26, 2009, 82 pages.

Wilton et al., "Antisense Oligonucleotides for Inducing Exon Skipping and Methods of Use Thereof," U.S. Appl. No. 12/837,356, filed Jul. 15, 2010, 94 pages.

Wilton et al., "Antisense Oligonucleotides for Inducing Exon Skipping and Methods of Use Thereof," U.S. Appl. No. 12/837,359, filed Jul. 15, 2010, 95 pages.

Wilton et al., "Antisense Oligonucleotides for Inducing Exon Skipping and Methods of Use Thereof," U.S. Appl. No. 12/860,078, filed Aug. 20, 2010, 91 pages.

\* cited by examiner

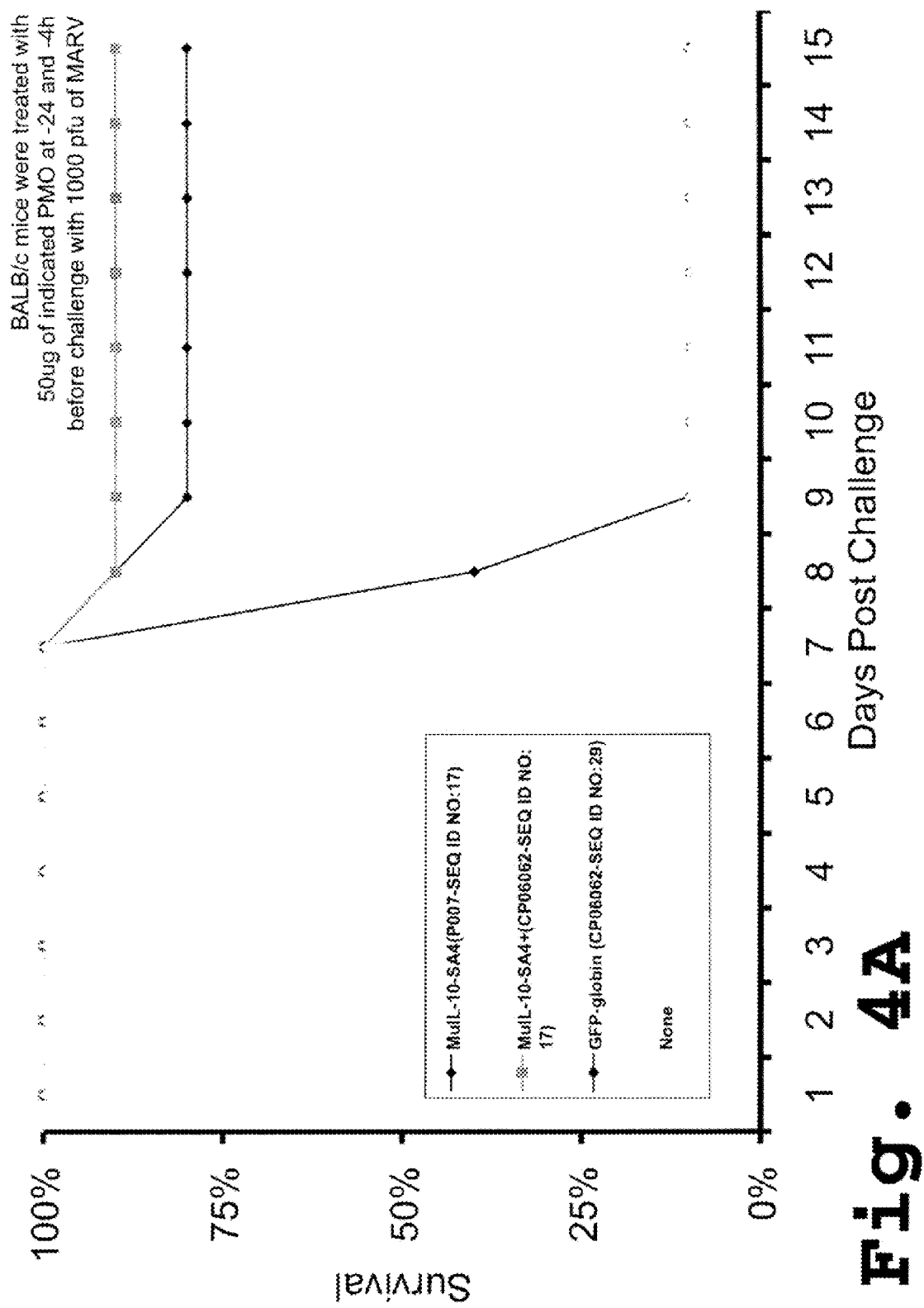

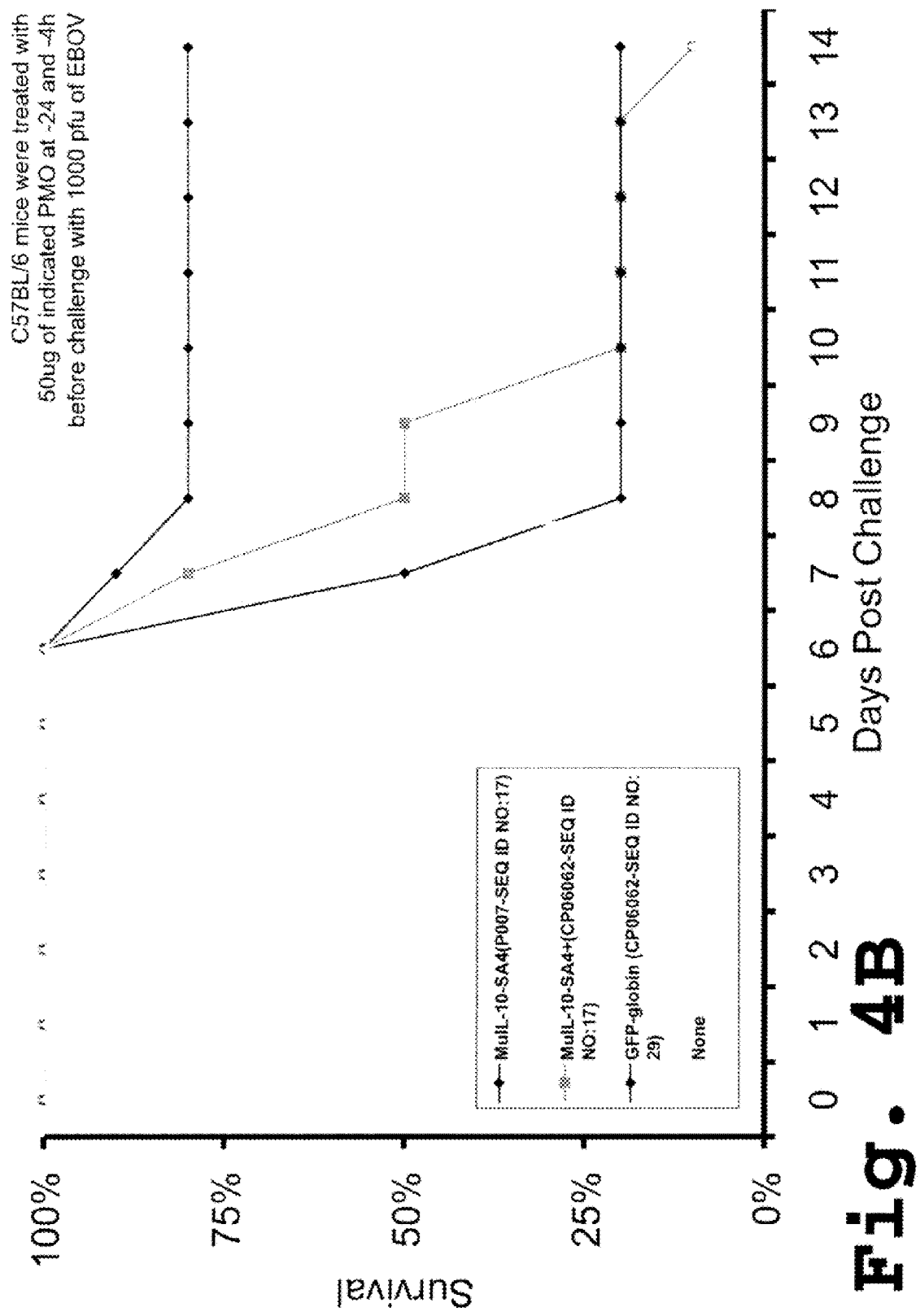

Fig. 5

SEQUENCE LISTING

<160> NUMBER OF SEQ ID NOS: 42

<210> SEQ ID NO 1
<211> LENGTH: 50
<212> TYPE: DNA
<213> ORGANISM: Homo sapiens

<400> SEQUENCE: 1
caagacagac ttgcaaaaga aggcatgcac agctcagcac tgctctgttg    50

<210> SEQ ID NO 2
<211> LENGTH: 25
<212> TYPE: DNA
<213> ORGANISM: Homo sapiens

<400> SEQUENCE: 2
caaatgaagg atcagctgga caact    25

<210> SEQ ID NO 3
<211> LENGTH: 50
<212> TYPE: DNA
<213> ORGANISM: Homo sapiens

<400> SEQUENCE: 3
cattctcctt tgttcttcc tgcagcaaat gaaggatcag ctggacaact                50

<210> SEQ ID NO 4
<211> LENGTH: 50
<212> TYPE: DNA
<213> ORGANISM: Homo sapiens

<400> SEQUENCE: 4
actcaccttt ggctcctgcc cttagggtta cctgggttgc caagccttgt                50

<210> SEQ ID NO 5
<211> LENGTH: 25
<212> TYPE: DNA
<213> ORGANISM: Homo sapiens

<400> SEQUENCE: 5
catcgatttc ttccctgtga aaaca                                            25

<210> SEQ ID NO 6
<211> LENGTH: 1613
<212> TYPE: DNA
<213> ORGANISM: Homo sapiens

<400> SEQUENCE: 6
tcattctcct tttgttcttc ctgcagcaaa tgaaggatca gctggacaac ttgttgttaa      60
aggagtcctt gctggaggac tttaaggtga gagcaggggc ggggtgctgg ggagtgtgc      120 agcatgatta agggaaggga gactctgctt cctgattgca gggaattggg tttgtttcct    180
tcgctttgaa aaggagaagt gggaagatgt taactcagca catccagcag ccagagggtt    240
tacaaagggc tcagtccctt cggggaggct tctggtgaag gaggatcgct agaaccaagc    300
tgtcctctta agctagttgc agcagcccct cctcccagcc acctccgcca atctctcact    360 caccttttggc tcctgccctt agggttacct gggttgccaa gccttgtctg agatgatcca    420
gttttacctg gaggaggtga tgccccaagc tgagaaccaa gacccagaca tcaaggcgca    480
tgtgaactcc ctgggggaga acctgaagac cctcaggctg aggctacggc gctgtgtaag    540
tagcagatca gttttttccc ttgcagctgc cccaaaaata ccatctccta cagaccagca    600
gggacactca catccacaga cacagcaaag acacagactg gcagagctag ctgtaaatga    660
ggaaagactc ctggagtcag atctcttgct catttctctt tgagcaggcg ttggggtgg    720 ctgctaggca tttacatgtg aaatttgcaa acagctttcc tgttatttgt gagtcatttg    780
tgggttatta actactcccc tctctcttca taaaggagc ccagagcttc agtcaggcct    840
ccactgcctc tttgtaacta daccctgggc ggggagctaa ggttcccaag cagaggaaac    900
atcattcacc tcttttaatc tcaatgtttt gaaagcaaag ctctaagaag gcccaattg    960 actgacagga tttcccctgg cattttagaa gggacaaggg ggctattcat ccccaggcta   1020
gtgtctatga gtaattcctc caggtaattt atttctccaa ctgaaatgat gccctcacta   1080
ctaatggttt cccctgttct gtcaccaata ttggaaaatc agttggtgtc tatttgtagg   1140
acaaggctat gtgaagggtt tggtcccagt agcttccctc ctcagatgct tagaagtgtt   1200
cctcggtggc tgtgactgac ggggaggaac aggagagaga ggcagaaaag acaggctga   1260

```
agaatgcctc gctcagcact gcaggagata ctgtagagtt ctgggggagg aaggaatccc    1320
aagacctggg ttgtcatcca agccttgcaa acatcttgga gtgagtcctg gagaaataca    1380
tttaactccc agggccatgg aagcagggct cagttctctc tgggagctgt gaggcaaggc    1440
atttggataa atctggcctc ctcatgatgc caccagcttg tccctaagt gtgatggaca     1500 tggagctgga agccaggatc accaacactt tctcttttct tccacagcat cgatttcttc    1560
cctgtgaaaa caagagcaag gccgtggagc aggtgaagaa tgcctttaat aag           1613

<210> SEQ ID NO 7
<211> LENGTH: 50
<212> TYPE: DNA
<213> ORGANISM: Homo sapiens

<400> SEQUENCE: 7
cagatccacg ctggctccgt gcgccatggt cacccacagc aagtttcccg               50

<210> SEQ ID NO 8
<211> LENGTH: 25
<212> TYPE: DNA
<213> ORGANISM: Homo sapiens

<400> SEQUENCE: 8
cgcgctcgcg ccttcctctc cgcag                                          25

<210> SEQ ID NO 9
<211> LENGTH: 50
<212> TYPE: DNA
<213> ORGANISM: Homo sapiens

<400> SEQUENCE: 9
ccccggacga tgcggcgcgc ccaggatgct gccgtgcctc gtagtgctgc                50

<210> SEQ ID NO 10
<211> LENGTH: 25
<212> TYPE: DNA
<213> ORGANISM: Homo sapiens

<400> SEQUENCE: 10
gtggtactga cactcttctc cccag                                          25

<210> SEQ ID NO 11
<211> LENGTH: 25
<212> TYPE: DNA
<213> ORGANISM: Homo sapiens

<400> SEQUENCE: 11
caaacacatc tctctgggcc tgcag                                          25

<210> SEQ ID NO 12
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 12
cagtgctgag ctgtgcatgc c                                              21

<210> SEQ ID NO 13
<211> LENGTH: 21
<212> TYPE: DNA
<213> ORGANISM: Artificial Sequence
<220> FEATURE:
```

```
<223> OTHER INFORMATION: Synthetic oligonucleotide

<400> SEQUENCE: 13
gtccagctga tccttcattt g                                              21

<210> SEQ ID NO 14
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 14
tcatctcaga caaggcttgg c                                              21

<210> SEQ ID NO 15
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 15
cttaaagtcc tccagcaagg ac                                             22

<210> SEQ ID NO 16
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 16
tttcacaggg aagaaatcga tg                                             22

<210> SEQ ID NO 17
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 17
ggagaaatcg atgctgaaga a                                              21

<210> SEQ ID NO 18
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 18
gtccagctgg tcctttgtgt t                                              21

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19
gcaaacgcga caacatcctg                                                20

<210> SEQ ID NO 20
```

```
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 20
aagggcttgg cagttctgtc c                                              21

<210> SEQ ID NO 21
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 21
tcaggttggt cacagtgaaa t                                              21

<210> SEQ ID NO 22
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 22
ttgctgtggg tgaccatggc g                                              21

<210> SEQ ID NO 23
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 23
gccgctaccg catcccgggg a                                              21

<210> SEQ ID NO 24
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 24
ctacgaggca cggcagcatc ctg                                            23

<210> SEQ ID NO 25
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 25
cggagggctg ggcagctctg tcc                                            23

<210> SEQ ID NO 26
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 26
```

-continued

```
gatgacgttg gtcacggtga aat                                         23

<210> SEQ ID NO 27
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 27
cttgctgtgg gtgaccatgg cgc                                         23

<210> SEQ ID NO 28
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 28
gccgctaccg catcccgggg gg                                          22

<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 29
agtctcgact tgctacctca                                             20

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 30
tgctattacc ttaacccaga                                             20

<210> SEQ ID NO 31
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 31
caacctgcct aacatgcttc                                             20

<210> SEQ ID NO 32
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 32
tcttcattgt catgtaggct tc                                          22

<210> SEQ ID NO 33
<211> LENGTH: 20
<212> TYPE: DNA
<213> ORGANISM: Artificial Sequence
<220> FEATURE:
```

```
<223> OTHER INFORMATION: Synthetic oligonucleotide

<400> SEQUENCE: 33
ggaagacaat aactgcaccc                                                    20

<210> SEQ ID NO 34
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 34
cattcatggc cttgtagaca c                                                  21

<210> SEQ ID NO 35
<211> LENGTH: 13
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (3), (6), (9), (12)
<223> OTHER INFORMATION: Xaa is 6-aminohexanoic acid
<220> FEATURE:
<221> NAME/KEY: MOD_RES
<222> LOCATION: (13)
<223> OTHER INFORMATION: Xaa is beta-alanine

<400> SEQUENCE: 35

Arg Arg Xaa Arg Arg Xaa Arg Arg Xaa Arg Arg Xaa Xaa
 1               5                  10

<210> SEQ ID NO 36
<211> LENGTH: 14
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (2), (5), (8), (11), (13)
<223> OTHER INFORMATION: Xaa is 6-aminohexanoic acid
<220> FEATURE:
<221> NAME/KEY: MOD_RES
<222> LOCATION: (14)
<223> OTHER INFORMATION: Xaa is beta-alanine

<400> SEQUENCE: 36

Arg Xaa Arg Arg Xaa Arg Arg Xaa Arg Arg Xaa Arg Xaa Xaa
 1               5                  10

<210> SEQ ID NO 37
<211> LENGTH: 14
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (1), (4), (7), (10), (13)
<223> OTHER INFORMATION: Xaa is 6-aminohexanoic acid
<220> FEATURE:
<221> NAME/KEY: MOD_RES
<222> LOCATION: (14)
<223> OTHER INFORMATION: Xaa is beta-alanine

<400> SEQUENCE: 37

Xaa Arg Arg Xaa Arg Arg Xaa Arg Arg Xaa Arg Arg Xaa Xaa
 1               5                  10
```

```
<210> SEQ ID NO 38
<211> LENGTH: 13
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (2), (4), (6), (8), (10), (12)
<223> OTHER INFORMATION: Xaa is 6-aminohexanoic acid
<220> FEATURE:
<221> NAME/KEY: MOD_RES
<222> LOCATION: (13)
<223> OTHER INFORMATION: Xaa is beta-alanine

<400> SEQUENCE: 38

Arg Xaa Arg Xaa Arg Xaa Arg Xaa Arg Xaa Arg Xaa Xaa
 1               5                  10

<210> SEQ ID NO 39
<211> LENGTH: 15
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (2), (4), (6), (8), (10), (12), (14)
<223> OTHER INFORMATION: Xaa is 6-aminohexanoic acid
<220> FEATURE:
<221> NAME/KEY: MOD_RES
<222> LOCATION: (15)
<223> OTHER INFORMATION: Xaa is beta-alanine

<400> SEQUENCE: 39

Arg Xaa Arg Xaa Arg Xaa Arg Xaa Arg Xaa Arg Xaa Arg Xaa Xaa
 1               5                  10                  15

<210> SEQ ID NO 40
<211> LENGTH: 11
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (2), (5), (8), (10)
<223> OTHER INFORMATION: Xaa is 6-aminohexanoic acid
<220> FEATURE:
<221> NAME/KEY: MOD_RES
<222> LOCATION: (11)
<223> OTHER INFORMATION: Xaa is beta-alanine

<400> SEQUENCE: 40

Arg Xaa Arg Arg Xaa Arg Arg Xaa Arg Xaa Xaa
 1               5                  10

<210> SEQ ID NO 41
<211> LENGTH: 14
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (2), (8), (13)
<223> OTHER INFORMATION: Xaa is 6-aminohexanoic acid
<220> FEATURE:
<221> NAME/KEY: MOD_RES
<222> LOCATION: (5), (11), (14)
<223> OTHER INFORMATION: Xaa is beta-alanine
```

```
<400> SEQUENCE: 41

Arg Xaa Arg Arg Xaa Arg Arg Xaa Arg Arg Xaa Arg Xaa Xaa
 1               5                  10

<210> SEQ ID NO 42
<211> LENGTH: 17
<212> TYPE: PRT
<213> ORGANISM: Artificial Sequence
<220> FEATURE:
<223> OTHER INFORMATION: Synthetic arginine-rich peptide
<220> FEATURE:
<221> NAME/KEY: MOD_RES
<222> LOCATION: (8), (16)
<223> OTHER INFORMATION: Xaa is 6-aminohexanoic acid
<220> FEATURE:
<221> NAME/KEY: MOD_RES
<222> LOCATION: (2), (4), (6), (10), (12), (14), (17)
<223> OTHER INFORMATION: Xaa is beta-alanine

<400> SEQUENCE: 42

Arg Xaa Arg Xaa Arg Xaa Arg Xaa Arg Xaa Arg Xaa Arg Xaa Arg Xaa
 1               5                  10                  15

Xaa
```

IMMUNOMODULATORY AGENTS AND METHODS OF USE

This patent application claims the benefit of priority to U.S. Patent Application No. 61/009,464 filed on Dec. 28, 2007, which is incorporated in its entirety herein by reference.

FIELD OF THE INVENTION

The present invention relates to methods and antisense compounds for producing enhanced immune responsiveness in a patient, e.g., for enhancing antiviral immunity or in combination with a vaccine against a pathogenic infectious disease or cancer, by suppressing expression of functional Interleukin 10 (IL-10) or IL-10 signal transduction.

REFERENCES

The following reference are cited in the Background or Methods sections of this application.

Akdis, C. A. and K. Blaser (2001). "Mechanisms of interleukin-10-mediated immune suppression." *Immunology* 103 (2): 131-6.

Banchereau, J. and A. K. Palucka (2005). "Dendritic cells as therapeutic vaccines against cancer." *Nat Rev Immunol* 5(4): 296-306.

Barcova, M., L. Kacani, et al. (1998). "gp41 envelope protein of human immunodeficiency virus induces interleukin (IL)-10 in monocytes, but not in B, T, or NK cells, leading to reduced IL-2 and interferon-gamma production." *J Infect Dis* 177(4): 905-13.

Biswas, P. S., V. Pedicord, et al. (2007). "Pathogen-specific CD8 T cell responses are directly inhibited by IL-10." *J Immunol* 179(7): 4520-8.

Boland, A. and G. R. Cornelis (1998). "Role of YopP in suppression of tumor necrosis factor alpha release by macrophages during *Yersinia* infection." *Infect Immun* 66(5): 1878-84.

Boussiotis, V. A., E. Y. Tsai, et al. (2000). "IL-10-producing T cells suppress immune responses in anergic tuberculosis patients." *J Clin Invest* 105(9): 1317-25.

Brady, M. T., A. J. MacDonald, et al. (2003). "Hepatitis C virus non-structural protein 4 suppresses Th1 responses by stimulating IL-10 production from monocytes." *Eur J Immunol* 33(12): 3448-57.

Bray, M., K. Davis, et al. (1998). "A mouse model for evaluation of prophylaxis and therapy of Ebola hemorrhagic fever." *J Infect Dis* 178(3): 651-61.

Brooks, D. G., M. J. Trifilo, et al. (2006). "Interleukin-10 determines viral clearance or persistence in vivo." *Nat Med* 12(11): 1301-9.

Cappuccio, A., F. Castiglione, et al. (2007). "Determination of the optimal therapeutic protocols in cancer immunotherapy." *Math Biosci* 209(1): 1-13.

Cornelis, G. R. and G. Denecker (2001). "*Yersinia* lead SUMO attack." *Nat Med* 7(1): 21-3.

Crooke, S. T. (2001). *Antisense Drug Technology: Principles, Strategies, and Applications*. New York, Marcel Dekker.

Dercamp, C., K. Chemin, et al. (2005). "Distinct and overlapping roles of interleukin-10 and CD25+ regulatory T cells in the inhibition of antitumor CD8 T-cell responses." *Cancer Res* 65(18): 8479-86.

Ejrnaes, M., C. M. Filippi, et al. (2006). "Resolution of a chronic viral infection after interleukin-10 receptor blockade." *J. Exp. Med.* 203(11): 2461-2472.

Encke, J., J. Findeklee, et al. (2005). "Prophylactic and therapeutic vaccination with dendritic cells against hepatitis C virus infection." *Clin Exp Immunol* 142(2): 362-9.

Fleming, S. B., C. A. McCaughan, et al. (1997). "A homolog of interleukin-10 is encoded by the poxvirus orf virus." *J Virol* 71(6): 4857-61.

Gong, J. H., M. Zhang, et al. (1996). "Interleukin-10 down-regulates *Mycobacterium tuberculosis*-induced Th1 responses and CTLA-4 expression." *Infect Immun* 64(3): 913-8.

Guerrero-Plata, A., A. Casola, et al. (2006). "Differential response of dendritic cells to human metapneumovirus and respiratory syncytial virus." *Am J Respir Cell Mol Biol* 34(3): 320-9.

Igietseme, J. U., G. A. Ananaba, et al. (2000). "Suppression of Endogenous IL-10 Gene Expression in Dendritic Cells Enhances Antigen Presentation for Specific Th1 Induction: Potential for Cellular Vaccine Development." *J Immunol* 164(8): 42124219.

Jacobs, M., N. Brown, et al. (2000). "Increased resistance to mycobacterial infection in the absence of interleukin-10." *Immunology* 100(4): 494-501.

Kornbluth, R. S, and G. W. Stone (2006). "Immunostimulatory combinations: designing the next generation of vaccine adjuvants." *J Leukoc Biol* 80(5): 1084-102.

Koutsonikolis, A., S. Haraguchi, et al. (1997). "HIV-1 recombinant gp41 induces IL-10 expression and production in peripheral blood monocytes but not in T-lymphocytes." *Immunol Lett* 55(2): 109-13.

Liu, G., H. Ng, et al. (2004). "Small interference RNA modulation of IL-10 in human monocyte-derived dendritic cells enhances the Th1 response." *Eur J Immunol* 34(6): 1680-7.

Marin-Serrano, E., C. Rodriguez-Ramos, et al. (2006). "Modulation of the anti-inflammatory interleukin 10 and of proapoptotic IL-18 in patients with chronic hepatitis C treated with interferon alpha and ribavirin." *J Viral Hepat* 13(4): 230-4.

Marshall, N. B., S. K. Oda, et al. (2007). "Arginine-rich cell-penetrating peptides facilitate delivery of antisense oligomers into murine leukocytes and alter pre-mRNA splicing." *Journal of Immunological Methods* 325(1-2): 114-126.

Miyada, C. G. and R. B. Wallace (1987). "Oligonucleotide hybridization techniques." *Methods Enzymol* 154: 94-107.

Moore, K. W., R. de Waal Malefyt, et al. (2001). "Interleukin-10 and the interleukin-10 receptor." *Annu Rev Immunol* 19: 683-765.

Mocellin, S., G. A. Ohnmacht, et al. (2001). "Kinetics of cytokine expression in melanoma metastases classifies immune responsiveness." *Int J Cancer* 93(2): 236-42.

Murray, P. J. and R. A. Young (1999). "Increased antimycobacterial immunity in interleukin-10-deficient mice." *Infect Immun* 67(6): 3087-95.

Nielsen, E. (2006). "RNA targeting using peptide nucleic acid." *Handb Exp Pharmacol* (173): 395403.

Nigou, J., C. Zelle-Rieser, et al. (2001). "Mannosylated lipoarabinomannans inhibit IL-12 production by human dendritic cells: evidence for a negative signal delivered through the mannose receptor." *J Immunol* 166(12): 7477-85.

Oh, J. H., C. S. Yang, et al. (2007). "Polymorphisms of interleukin-10 and tumour necrosis factor-alpha genes are associated with newly diagnosed and recurrent pulmonary tuberculosis." *Respirology* 12(4): 594-8.

Oral, H. B., F. Budak, et al. (2006). "Interleukin-10 (IL-10) gene polymorphism as a potential host susceptibility factor in tuberculosis." *Cytokine* 35(3-4): 143-7.

Orsilles, M. A., E. Pieri, et al. (2006). "IL-2 and IL-10 serum levels in HIV-1-infected patients with or without active antiretroviral therapy." *Apmis* 114(1): 55-60.

Rigopoulou, E. I., W. G. H. Abbott, et al. (2005). "Blocking of interleukin-10 receptor—a novel approach to stimulate T-helper cell type 1 responses to hepatitis C virus." *Clinical Immunology* 117(1): 57-64.

Romani, N., S. Gruner, et al. (1994). "Proliferating dendritic cell progenitors in human blood." *J Exp Med* 180(1): 83-93.

Schols, D. and E. De. Clercq (1996). "Human immunodeficiency virus type 1 gp120 induces energy in human peripheral blood lymphocytes by inducing interleukin-10 production." *J Virol* 70(8): 4953-60.

Stockl, J., H. Vetr, et al. (1999). "Human major group rhinoviruses downmodulate the accessory function of monocytes by inducing IL-10." *J Clin Invest* 104(7): 957-65.

Summerton, J. and D. Weller (1997). "Morpholino antisense oligomers: design, preparation, and properties." *Antisense Nucleic Acid Drug Dev* 7(3): 187-95.

Suzuki, T., H. Tahara, et al. (1995). "Viral interleukin 10 (IL-10), the human herpes virus 4 cellular IL-10 homologue, induces local anergy to allogeneic and syngeneic tumors." *J Exp Med* 182(2): 477-86.

Taoufik, Y., O. Lantz, et al. (1997). "Human immunodeficiency virus gp120 inhibits interleukin-12 secretion by human monocytes: an indirect interleukin-10-mediated effect." *Blood* 89(8): 2842-8.

Tufariello, J., S. Cho, et al. (1994). "The adenovirus E3 14.7-kilodalton protein which inhibits cytolysis by tumor necrosis factor increases the virulence of vaccinia virus in a murine pneumonia model." *J Virol* 68(1): 453-62.

Tufariello, J. M., S. Cho, et al. (1994). "Adenovirus E3 14.7-kilodalton protein, an antagonist of tumor necrosis factor cytolysis, increases the virulence of vaccinia virus in severe combined immunodeficient mice." *Proc Natl Acad Sci USA* 91(23): 10987-91.

Van Gulck, E. R. A., P. Ponsaerts, et al. (2006). "Efficient stimulation of HIV-1-specific T cells using dendritic cells electroporated with mRNA encoding autologous HIV-1 Gag and Env proteins." *Blood* 107(5): 1818-1827.

Vicari, A. P., C. Chiodoni, et al. (2002). "Reversal of tumor-induced dendritic cell paralysis by CpG immunostimulatory oligonucleotide and anti-interleukin 10 receptor antibody." *J Exp Med* 196(4): 541-9.

Vockerodt, M., B. Haier, et al. (2001). "The Epstein-Barr virus latent membrane protein 1 induces interleukin-10 in Burkitt's lymphoma cells but not in Hodgkin's cells involving the p38/SAPK2 pathway." *Virology* 280(2): 183-98.

Tufariello, D. H., M. Li, et al. (2007). "A combined DNA vaccine enhances protective immunity against *Mycobacterium tuberculosis* and *Brucella abortus* in the presence of an IL-12 expression vector." *Vaccine* 25(37-38): 6744-54.

BACKGROUND OF THE INVENTION

There is a variety of evidence that pathogens may be able to suppress the body's defenses, particularly immune defenses, against infection by up- or down-regulating specific cytokines that play a role in the immune response. For example, *Yersinia* infection suppresses TNF-alpha release by macrophages (Boland and Cornelis 1998; Cornelis and Denecker 2001); the adenovirus E3 protein is an antagonist of TNF cytolysis (Tufariello, Cho et al. 1994; Tufariello, Cho et al. 1994); and *Mycobacterium tuberculosis* inhibits LPS-induced IL-12 production by human dendritic cells (Nigou, Zelle-Rieser et al. 2001).

Multiple pathogens, particularly intracellular pathogens, appear to up-regulate IL-10 production, as a strategy for inhibiting removal of the pathogen by the immune system. (Moore, de Waal Malefyt et al. 2001). Stockl et al. showed that human rhinoviruses (HRV) suppress the accessory function of monocytes by inducing IL-10 (Stockl, Vetr et al. 1999). Respiratory syncytial virus (RSV) causes an excessive IL-10 response leading to downregulation of antiviral defense mechanisms and reduced elimination of respiratory pathogens (Miyada and Wallace 1987; Guerrero-Plata, Casola et al. 2006). Fleming et al show that an IL-10 homologue is encoded by the poxvirus orf virus (Fleming, McCaughan et al. 1997). Viral homologues of IL-10 have also been found in Epstein-Barr virus (Suzuki, Tahara et al. 1995) and equine herpes virus. Epstein-Barr virus (EBV) also induces IL-10 expression in Burkitt's lymphoma cells (Vockerodt, Haier et al. 2001). Specifically, EBV encodes a human IL-10 homolog as well as the EBV latent protein-1 that induces IL-10 and both of these EBV factors are thought to facilitate viral survival and pathogenesis through IL-10's immune suppressive activity.

The human immunodeficiency virus (HIV) envelope gene products have been shown to induce IL-10 expression in monocytes (Koutsonikolis, Haraguchi et al. 1997; Taoufik, Lantz et al. 1997; Barcova, Kacani et al. 1998) and to induce anergy in human peripheral blood lymphocytes (Schols and De Clercq 1996). These findings indicate that IL-10 plays an important role in the inhibitory effect of gp120 on PBMC proliferation and could contribute to the depressed immune responses associated with human immunodeficiency virus infection and thus have important implications for immunotherapeutic strategies to slow down disease progression in AIDS. Furthermore, a negative correlation was observed between IL-10 serum levels and CD4+ T-cell counts in HAART naïve, HIV-infected patients and that the increase in IL-10 serum levels in HIV-1-infected patients is associated with the progression of immune deficiency (Orsilles, Pieri et al. 2006).

IL-10 has been shown to play a critical role in a murine model of *M. bovis Bacillus* Calmifte-Guerin (BCG) infection since IL-10 over-expression enhanced bacilli growth and an IL-10 knock-out mouse showed increased anti-mycobacterial immunity, lowered BCG load and increased levels of pro-inflamatory cytokines (Murray and Young 1999). This suggests that IL-10 is an inhibitor of early mycobacterial clearance and negatively regulates numerous macrophage functions as well as playing a role in down-regulating the general inflammatory response (Jacobs, Brown et al. 2000). Clinical data also lend support for IL-10 in tuberculosis pathogenesis, (Gong, Zhang et al. 1996) lending further support that L-10 mediates the anergy seen in patients with active tuberculosis (Boussiotis, Tsai et al. 2000). Furthermore, a polymorphic allele of the IL-10 gene plays an important role in determining susceptibility to TB (Oral, Budak et al. 2006; Oh, Yang et al. 2007).

IL-10 may also be involved in susceptibility to several other human pathogens including *Listeria monocytogenes*, lymphocytic choriomeningitis virus (LCMV) and Hepatitis C virus (HCV) infections. Biswas, et al demonstrated that IL-10 inhibits CD8 T cell responses by restricting T cell expansion during primary and memory responses to *L. monocytogenes* infection (Biswas, Pedicord et al. 2007). Ejrnaes, et al show that IL-10 production is drastically increased in mice persistently infected with LCMV and that in vivo blockade of the IL-10 receptor (IL-10R) with a neutralizing antibody resulted in rapid resolution of the persistent infection (Ejrnaes, Filippi et al. 2006). The HCV nonstructural protein 4 (NS4) induces peripheral blood mononuclear cells (PBMC) to secrete IL-10 and inhibits IL-12 production by PBMC in response to LPS and IFN-gamma (Brady, MacDonald et al. 2003). Increased concentrations of IL-10 in chronic HCV-infected, interferon alpha and ribavirin nonresponder patients compared to baseline IL-10 levels in those with a complete response and suggest that IL-10 may inhibit Th1 cells and the host immune response against HCV (Marin-Serrano, Rodriguez-Ramos et al. 2006). These results suggest that HCV subverts cellular immunity by inducing IL-10 and inhibiting IL-12 production by monocytes, which in turn inhibits the activation of DC that drive the differentiation of Th1 cells. Furthermore, therapeutic administration of an antibody that blocks the IL-10 receptor restored T-cell function and eliminated a persistent LCMV infection (Brooks, Trifilo et al. 2006). Along these same lines, a monoclonal antibody-induced blockade of IL-10R increases the CD4+ T-cell responses to HCV antigens and suggests that IL-10R blockade with a human monoclonal antibody has the potential to alter the host immune response to HCV (Rigopoulou, Abbott et al. 2005).

IL-10 also is known to play a role in the development of cancer (Dercamp, Chemin et al. 2005). Elevated levels of IL-10 mRNA have been observed in immune-responsive versus non-responsive metastatic melanoma lesions (Mocellin, Ohnmacht et al. 2001). Dercamp, et al show that IL-10 and regulatory T cells ($T_{reg}$) act together to impair antitumor CD8+ T cell effector differentiation and induce tumor-induced antigen-specific anergy in CD8+ T cells (Dercamp, Chemin et al. 2005). Furthermore, treatment with a combination of anti-IL-10R monoclonal antibody and toll-like receptor 9 ligands has been shown to be an effective antitumor therapeutic regimen (Vicari, Chiodoni et al. 2002).

It would thus be desirable to provide a therapeutic compound that is effective in suppressing functional IL-10, or IL-10 signal transduction as a treatment modality during infection, in the treatment of cancers in which IL-10 overproduction may subvert the body's ability to mount an immunological defense against the cancer, and as an adjunct for vaccines, to enhance immune responsiveness to the vaccine.

SUMMARY OF THE INVENTION

In one aspect, the invention includes a method of treating a mammalian subject infected with a pathogen which acts to up-regulate IL-10 during infection in a mammalian host, as evidenced by increased serum levels of IL-10. The method includes the step of administering to the subject, a therapeutically effective amount of an antisense composition containing an oligonucleotide compound that (i) is composed of morpholino subunits and phosphorus-containing intersubunit linkages joining a morpholino nitrogen of one subunit to a 5' exocyclic carbon of an adjacent subunit, (ii) is capable of uptake by monocytes, lymphocytes, and dendritic cells in a mammalian subject, (iii) contains between 1040 nucleotide bases, and (iv) has a base sequence effective to hybridize to at least 12 contiguous bases of a target sequence composed of 5'-end 25 bases of exon 2 or exon 4 of the preprocessed human IL-10 transcript contained within SEQ ID NO:6, and identified by SEQ ID NOS: 2 and 5, respectively. The target sequence to which the oligonucleotide compound hybridizes may be contained entirely within SEQ ID NOS:2 or 5.

The composition administered may contain a second oligonucleotide antisense compound having a base sequence effective to hybridize to at least 12 contiguous bases of another splice junction target sequence of the preprocessed human IL-10 transcript contained within SEQ ID NO: 6. For example, the composition may contain oligonucleotide compounds targeting both SEQ ID NOS: 2 and 5.

The oligonucleotide compound which is administered may be conjugated to an arginine-rich polypeptide effective to promote uptake of the compound into monocytes, lymphocytes, and dendritic cells. Exemplary peptides are those having the sequence defined by SEQ ID NO: 36 or SEQ ID NO: 40.

For use in treating a mammalian subject infected with a viral or bacterial pathogen which acts to up-regulate IL-10 during viral infection, the method may further include administering to the subject, an anti-viral or anti-bacterial compound, respectively, effective to inhibit replication of the viral or bacterial pathogen in the mammalian host.

In a related aspect for treating a mammalian subject infected with a pathogen which acts to up-regulate IL-10 during infection in a mammalian host, as evidenced by increased serum levels of IL-10, the oligonucleotide compound that is administered to the subject has properties (i)-(iii) above and a base sequence effective to hybridize to at least 12 contiguous bases of a target sequence containing one of: the SOCS3-AUG start-site region identified by SEQ ID NO:7; the SOCS3 exon-2 splice acceptor site region identified by SEQ ID NO:8; the IL10Ra-AUG start-site region identified by SEQ ID NO: 9; the exon-2 splice acceptor site region (IL10Ra Exon 2SA) identified by SEQ ID NO: 10; and the exon-6 splice acceptor site region (IL10Ra Exon 6SA) identified by SEQ ID NO: 11, where SOCS3 is the gene for human Suppressor of Cytokine Signaling-3, and IL10Ra is the gene for human IL-10 Receptor alpha subunit.

Another aspect of the invention includes treating a viral infection in a mammalian subject infected with a viral pathogen that encodes a viral IL-10 homolog (vIL-10). Viral infections included here include, for example, cytomegalovirus (CMV), Epstein Barr virus (EBV) Human Herpes virus species (HHV) and various human pox viruses including the orf poxvirus. The treatment in this aspect of the invention employs oligonucleotide compounds of the invention that target the IL-10 Receptor Alpha (IL10Ra) and Suppressor of Cytokine Signaling-3 genes, as described above.

The composition administered may contain a second oligonucleotide antisense compound having a base sequence effective to hybridize to at least 12 contiguous bases of a splice junction target sequence of the preprocessed human IL-10 transcript contained within SEQ ID NO:6, such as the regions identified by SEQ ID NOS:2 or 5.

In a related aspect, the invention provides a method of treating cancer characterized by an enhanced level of IL-10 expression, as evidenced by increased levels of IL-10 in the serum or extracellular environment of the cancer. The method includes the steps of administering to the individual, a therapeutically effective amount of one of more of the antisense oligonucleotide compounds described above targeting the human IL-10, SOCS3 and/or IL10Ra genes. The treatment is typically carried out as a combination therapy in which the above-described oligonucleotide compound is administered as an adjunct to an anti-neoplastic agent or other treatment modality, such as radiation treatment.

Also disclosed is a vaccine against a pathogen comprising (a) a pathogen antigenic component capable of eliciting an immune response against the pathogen, (b) one or more of the above-described an antisense oligonucleotide compounds having a base sequence effective to hybridize to at least 12 contiguous bases of a target sequence composed of 5'-end 25 bases of exon 2 or exon 4 of the preprocessed human IL-10 transcript contained within SEQ ID NO:6, and identified by SEQ ID NOS: 2 and 5, respectively, and (c) an adjuvant in which the antigenic component and antisense compound are formulated.

In a related aspect of the invention, there is provided a vaccine against a pathogen comprising (a) a pathogen antigenic component capable of eliciting an immune response against the pathogen, (b) one or more of the above-described an antisense oligonucleotide compounds having a base sequence effective to hybridize to at least 12 contiguous bases of a target sequence containing one of: the SOCS3-AUG start-site region identified by SEQ ID NO:7; the SOCS3 exon-2 splice acceptor site region identified by SEQ ID NO:8; the IL10Ra-AUG start-site region identified by SEQ ID NO: 9; the exon-2 splice acceptor site region (IL10Ra Exon 2SA) identified by SEQ ID NO: 10; and the exon-6 splice acceptor site region (IL10Ra Exon 6SA) identified by SEQ ID NO: 11; and (c) an adjuvant in which the antigenic component and antisense compound are formulated.

In still another aspect, the invention includes an antisense oligonucleotide compound that is: (i) composed of morpholino subunits and phosphorus-containing intersubunit linkages joining a morpholino nitrogen of one subunit to a 5' exocyclic carbon of an adjacent subunit, (ii) capable of uptake by monocytes, lymphocytes, and dendritic cells in a mammalian subject, (iii) containing between 10-40 nucleotide bases, and (iv) having a base sequence effective to hybridize to at least 12 contiguous bases of a target sequence composed of 5'-end 25 bases of exon 2 or exon 4 of the preprocessed human IL-10 transcript contained within SEQ ID NO:6, and identified by SEQ ID NOS: 2 and 5, respectively. The base sequence to which the oligonucleotide compound hybridizes may be contained entirely within SEQ ID NOS: 2 or 5. Exemplary oligonucleotide compound sequences include SEQ ID NOS: 13 and 16.

More generally, the compound may have a base sequence effective to hybridize to at least 12 contiguous bases of a splice-site target sequence contained within the pre-processed human IL-10 transcript contained within SEQ ID NO:6, where compound binding to the target sequence is effective block expression of a functional human IL-10 in IL-10 expressing cells, such as monocytes, lymphocytes, and dendritic cells, i.e., antigen presenting cells, exposed to the compound.

The compound may be conjugated to an arginine-rich polypeptide effective to promote uptake of the compound into lymphocytes. Exemplary peptides include those identified by the sequences SEQ ID NO: 36 or SEQ ID NO:40.

The intersubunit linkages linking the morpholino subunits in the compound may be phosphorodiamidate linkages having the structure:

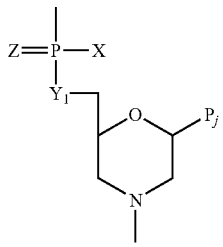

where $Y_1$=O, Z=O, Pj is a purine or pyrimidine base-pairing moiety effective to bind, by base-specific hydrogen bonding, to a base in a polynucleotide, and X is alkyl, alkoxy, thioalkoxy, or alkyl amino e.g., wherein X=$NR_2$, where each R is independently hydrogen or methyl. The above intersubunit linkages, which are uncharged, may be interspersed with linkages that are positively charged at physiological pH, where the total number of positively charged linkages is between 2 and no more than half of the total number of linkages. The positively charged linkages may have the above structure in which X is 1-piperazine.

Also disclosed is the use of the compound above for the treatment of a mammalian subject infected with a pathogen which acts to up-regulate IL-10 during infection in a mammalian host, as evidenced by increased serum levels of IL-10.

In another aspect, the invention includes an antisense composition comprising first and second antisense compounds of the type described above having, in the first compound, a base sequence effective to hybridize to at least 12 contiguous bases of the 5'-most 25 bases of exon 2 or exon 4 of the preprocessed human IL-10 transcript contained within SEQ ID NO:6, and in the second compound, a base sequence effective to hybridize to at least 12 contiguous bases of another splice-site target sequence of the preprocessed human IL-10 transcript contained within SEQ ID NO:6.

The first and second antisense compounds may have base sequences effective to hybridize to at least 12 contiguous bases of the 5'-most 25 bases of exon 2 and exon 4, respectively, of a human IL-10 transcript defined by SEQ ID NO: 6.

In a related aspect, the invention provides an oligonucleotide compound having properties (i)-(iii) above and a base sequence effective to hybridize to at least 12 contiguous bases of a target sequence containing one of: the SOCS3 AUG start-site region identified by SEQ ID NO:7; the SOCS3 exon-2 splice acceptor site region identified by SEQ ID NO:8; the IL10Ra-AUG start-site region identified by SEQ ID NO: 9; the exon-2 splice acceptor site region (IL10Ra Exon 2SA) identified by SEQ ID NO: 10; and the exon-6 splice acceptor site region (IL10Ra Exon 6SA) identified by SEQ ID NO: 11, where SOCS3 is the gene for human Suppressor of Cytokine Signaling-3, and IL10Ra is the gene for human IL-10 Receptor alpha subunit. Exemplary oligonucleotide sequences includes SEQ ID NOS: 24-28.

These and other objects and features of the invention will become more fully apparent when the following detailed description of the invention is read in conjunction with the accompanying drawings.

BRIEF DESCRIPTION OF THE DRAWINGS

FIGS. 4A-B show anti-IL-10 PPMO treatment protected 90 and 80% of mice (n=10) from lethal doses of Marburg virus and Ebola virus, respectively.

FIG. 5 shows the level of IL-10 expression in anti-IL-10 PPMO-treated PBMC (P007-HuIL-10-SA2; SEQ ID NO:36 conjugated to SEQ ID NO:13) after stimulation with HIV-1 gp120.

DETAILED DESCRIPTION OF THE INVENTION

I. Definitions

Figure 1A:
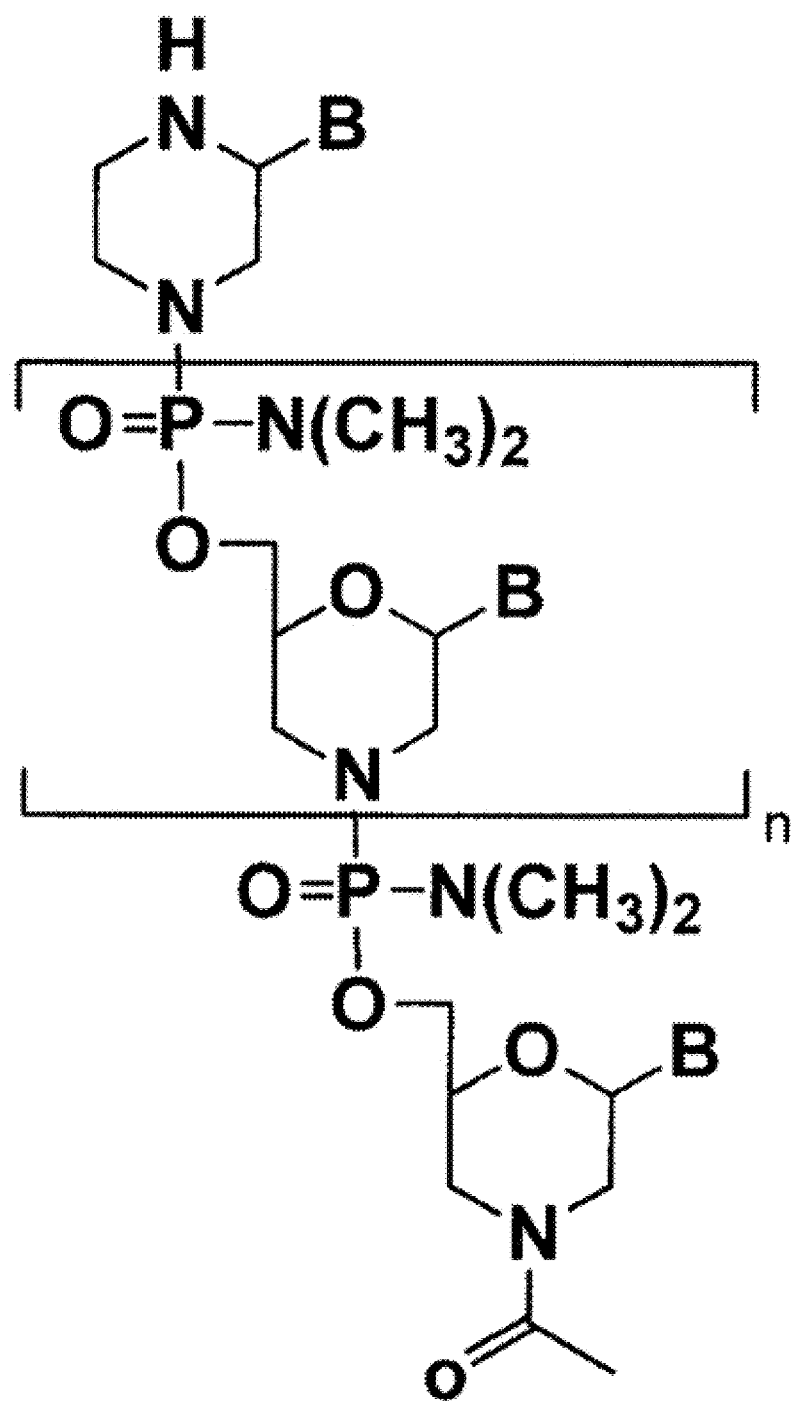
FIGS. 1A-C show exemplary structures of a phosphorodiamidate-linked morpholino oligomer (PMO), a peptide-conjugated PMO (PPMO), and a peptide-conjugated PMO having cationic intersubunit linkages (PPMO+), respectively. (Though multiple cationic linkage types are illustrated in FIG. 1C, a PMO+ or PPMO+ oligomer will typically include just one type of cationic linkage.)

The terms below, as used herein, have the following meanings, unless indicated otherwise:

The terms "antisense oligomer" or "antisense compound" are used interchangeably and refer to a sequence of subunits, each having a base carried on a backbone subunit composed of ribose or other pentose sugar or morpholino group, and where the backbone groups are linked by intersubunit linkages that allow the bases in the compound to hybridize to a target sequence in a nucleic acid (typically an RNA) by Watson-Crick base pairing, to form a nucleic acid:oligomer heteroduplex within the target sequence. The oligomer may have exact sequence complementarity to the target sequence or near complementarity. Such antisense compounds are designed to block or inhibit translation of the mRNA containing the target sequence or designed to block pre-mRNA processing (i.e., splicing) and may be said to be "directed to" a sequence with which it hybridizes.

A "morpholino oligomer" refers to a polymeric molecule having a backbone which supports bases capable of hydrogen bonding to typical polynucleotides, wherein the polymer lacks a pentose sugar backbone moiety, and more specifically a ribose backbone linked by phosphodiester bonds which is typical of nucleotides and nucleosides, but instead contains a ring nitrogen with coupling through the ring nitrogen. A preferred "morpholino" oligomer is composed of morpholino subunit structures linked together by phosphoramidate or phosphorodiamidate linkages, joining the morpholino nitrogen of one subunit to the 5' exocyclic carbon of an adjacent subunit, each subunit including a purine or pyrimidine base-pairing moiety effective to bind, by base-specific hydrogen bonding, to a base in a polynucleotide. Morpholino oligomers (including antisense oligomers) are detailed, for example, in co-owned U.S. Pat. Nos. 5,698,685, 5,217,866, 5,142,047, 5,034,506, 5,166,315, 5,185,444, 5,521,063, and 5,506,337, all of which are expressly incorporated by reference herein.

A "phosphoramidate" group comprises phosphorus having three attached oxygen atoms and one attached nitrogen atom, while a "phosphorodiamidate" group (see e.g. FIGS. 1A-B) comprises phosphorus having two attached oxygen atoms and two attached nitrogen atoms. In the uncharged or the cationic intersubunit linkages of the oligomers described herein, one nitrogen is always pendant to the backbone chain. The second nitrogen, in a phosphorodiamidate linkage, is typically the ring nitrogen in a morpholino ring structure (again, see FIGS. 1A-B). A phosphoramidate or phosphorodiamidate linkage may include a thiophosphoramidate or thiophosphorodiamidate linkage, respectively, in which one oxygen atom, typically the oxygen pendant to the backbone in the oligomers described herein, is replaced with sulfur.

The terms "uncharged" and "cationic" are used herein to refer to the predominant charge state of a backbone linking groups in an antisense compound at near-neutral pH, e.g. about 6 to 8. Preferably, the term refers to the predominant state of the chemical moiety at physiological pH, that is, about 7.4. An antisense compound is "substantially uncharged" if all or all but a small number, e.g., 1-3, of the backbone linkages in the compound are uncharged.

"Lower alkyl" refers to an alkyl radical of one to six carbon atoms, as exemplified by methyl, ethyl, n-butyl, i-butyl, t-butyl, isoamyl, n-pentyl, and isopentyl. In selected embodiments, a "lower alkyl" group has one to four carbon atoms, or 1-2 carbon atoms; i.e. methyl or ethyl. Analogously, "lower alkenyl" refers to an alkenyl radical of two to six, preferably three or four, carbon atoms, as exemplified by allyl and butenyl.

Polynucleotides are described as "complementary" to one another when hybridization occurs in an antiparallel configuration between two single-stranded polynucleotides. Complementarity (the degree that one polynucleotide is complementary with another) is quantifiable in terms of the proportion of bases in opposing strands that are expected to form hydrogen bonds with each other, according to generally accepted base-pairing rules.

A first sequence is an "antisense sequence" with respect to a second sequence if a polynucleotide whose sequence is the first sequence specifically binds to, or specifically hybridizes with, the second polynucleotide sequence under physiological conditions.

The term "targeting sequence" is the sequence in the oligonucleotide analog that is complementary (meaning, in addition, substantially complementary) to the target sequence in a pre-processed mRNA transcript, and specifically the pre-processed mRNA transcript of human IL-10 defined by SEQ ID NO:6. The entire targeting sequence, or only a portion, of the compound may be complementary to the target sequence. For example, in an antisense compound having 20 bases, only 12-14 may be targeting sequences. Typically, the targeting sequence is formed of contiguous bases in the compound, but may alternatively be formed of non-contiguous sequences that when placed together, e.g., from opposite ends of the compound, constitute sequence that spans the target sequence.

Target and targeting sequences are described as "complementary" to one another when hybridization occurs in an antiparallel configuration. A targeting sequence may have "near" or "substantial" complementarity to the target sequence and still function for the purpose of the presently described methods, that is, still be "complementary." Preferably, the oligonucleotide analog compounds employed in the presently described methods have at most one mismatch with the target sequence out of 10 nucleotides, and preferably at most one mismatch out of 20. Alternatively, the antisense compounds employed have at least 90% sequence homology, and preferably at least 95% sequence homology, with the exemplary targeting sequences as designated herein. For purposes of complementary binding to an RNA target, and as discussed below, a guanine base may be complementary to either an adenine or uracil RNA base.

An oligonucleotide analog "specifically hybridizes" to a target polynucleotide if the oligomer hybridizes to the target under physiological conditions, with a $T_m$ substantially greater than 45° C., preferably at least 50° C., and typically 60° C.-80° C. or higher. Such hybridization preferably corresponds to stringent hybridization conditions. At a given ionic strength and pH, the $T_m$ is the temperature at which 50% of a target sequence hybridizes to a complementary polynucleotide. Again, such hybridization may occur with "near" or "substantial" complementary of the antisense compound to the target sequence, as well as with exact complementarity.

A "heteroduplex" refers to a duplex between an oligonucleotide analog and the complementary portion of a target RNA. A "nuclease-resistant heteroduplex" refers to a heteroduplex formed by the binding of an antisense compound to its complementary target, such that the heteroduplex is substantially resistant to in vivo degradation by intracellular and extracellular nucleases, such as RNAse H, which are capable of cutting double-stranded RNA/RNA or RNA/DNA complexes.

"Monocytes, lymphocytes, and dendritic cells" refer to three types of white blood cells of the immune system that produce IL-10 under specific conditions of immune challenge. The cell types have their common, textbook definitions.

Figure 6:
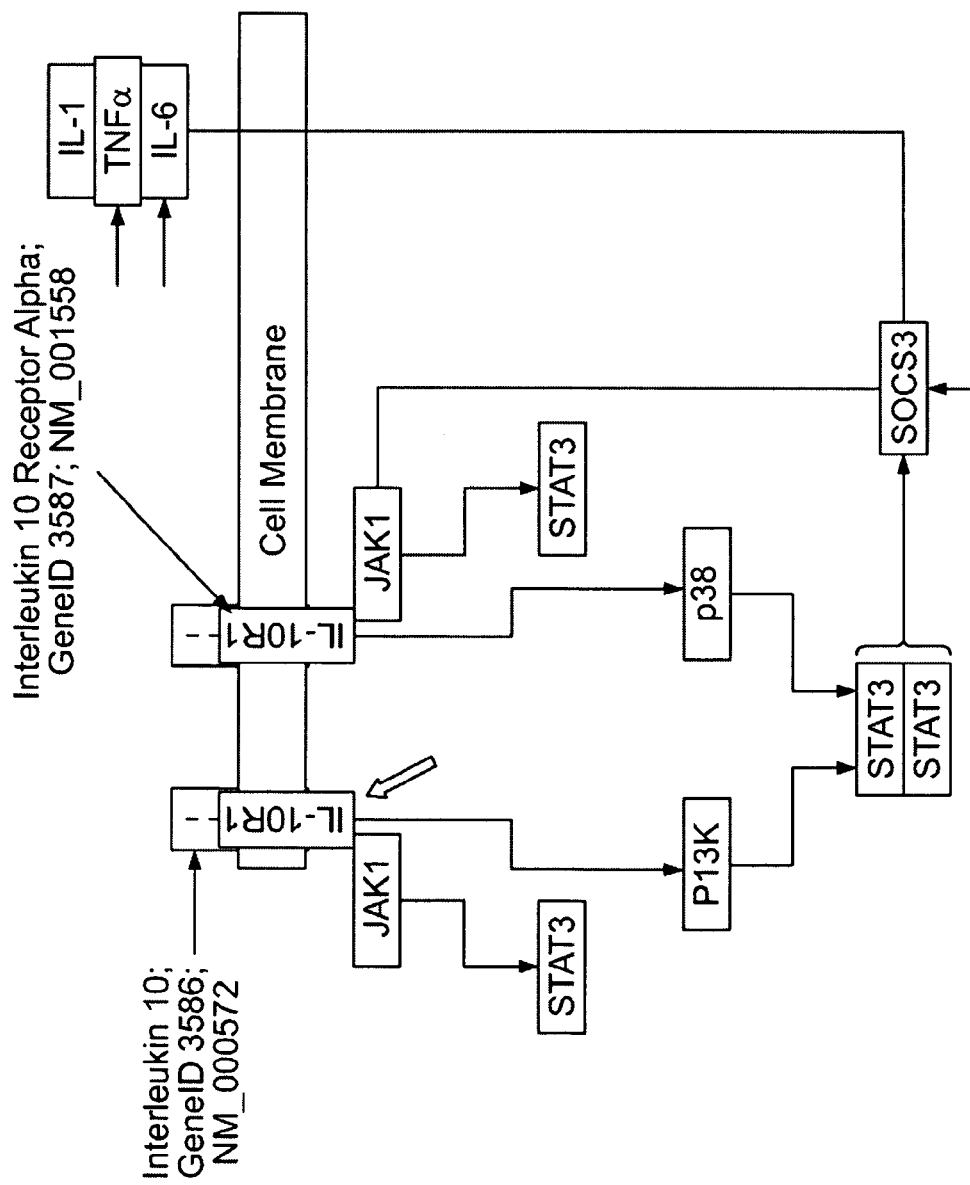
FIG. 6 shows the IL-10 signaling pathway and the targets that provide protection from lethal Ebola virus challenge (i.e., IL-10, IL10Ra and SOCS3) as described in Example 3.

The terms "IL-10 signaling pathway" and "IL-10 signal transduction pathway" are used interchangeably and refer to the cellular protein machinery that both detects IL-10 on the surface of cells (e.g., IL-10 receptors) and signals its presence to intracellular proteins that alter the phenotype of the IL-10 targeted cell (i.e., see FIG. 6).

An agent is "taken up by monocytes, lymphocytes, and dendritic cells in a mammalian subject" if the compound is taken up by these cells by passive transport across the cell membrane or by an active transport mechanism involving, for example, transport across the membrane by e.g. an ATP-dependent transport mechanism, or by "facilitated transport", referring to transport of antisense agents across the cell membrane by a transport mechanism that requires binding of the agent to a transport protein, which then facilitates passage of the bound agent across the membrane, or by cell membrane invagination. Uptake of the compound into the target cells may be confirmed, for example, by uptake of a fluoresceinated compound in the cells, An "amino acid subunit" is preferably an α-amino acid residue (—CO—CHR—NH—); it may also be a β- or other amino acid residue (e.g. —CO—CH$_2$CHR—NH—), where R is a side chain.

The term "naturally occurring amino acid" refers to an amino acid present in proteins found in nature. The term "non-natural amino acids" refers to those amino acids not present in proteins found in nature; examples include beta-alanine (®-Ala) and 6-aminohexanoic acid (Ahx).

An "effective amount" or "therapeutically effective amount" refers to an amount of antisense compound administered to a mammalian subject, either as a single dose or as part of a series of doses, which is effective to produce a desired therapeutic effect, such as reduced level of infection, or viral or bacterial titre in the bloodstream, or a reduction in tumor size.

"Treatment" of an individual (e.g. a mammal, such as a human) or a cell is any type of intervention used in an attempt to alter the natural course of the individual or cell. Treatment includes, but is not limited to, administration of a pharmaceutical composition, and may be performed either prophylactically or subsequent to the initiation of a pathologic event or contact with an etiologic agent.

II. Antisense Compound

A. Target and Targeting Sequences

A preferred antisense compound of the invention targets a splice-site target sequence contained within SEQ ID NO:6, the segment of the human IL-10 preprocessed mRNA transcript extending from 26 nucleotides of intron 1 immediately upstream of exon 2, all of exons 24 and the intervening introns 2 and 3. This target can also be described by the GenBank accession number: NT_021877.18, bases 460953 to 462565 (minus strand).

Splice-site target sequences contained within SEQ ID NO:6 include any contiguous sequence of bases, typically at least 12 to 22 or more contiguous bases, at which hybridization by an antisense oligonucleotide is effective to disrupt normal processing of a pre-processed IL-10 mRNA transcript into a processed mRNA that can be expressed as a mature (native) human IL-10 protein containing exon-2, exon-3, and exon-4 peptide segments. Exemplary splice-site target sequences include:

(i) sequences spanning a spice acceptor or splice donor junction that includes one of exons 2, 3, or 4, such as a target sequence contained within SEQ ID NOS:3 or 4 in Table 1 below, spanning the splice acceptor junctions (shown by the "/" mark) of exon 2 and exon 3, respectively;

(ii) a target region that is contained wholly within the 5'-end sequences of exon 2, 3, or 4, e.g., the 5'-most 25 bases in each exon, as exemplified by the 5' end most bases in SEQ ID NOS:2 and 4, respectively;

(iii) a branch site (A) in the middle of intron 2 or 3; and (iv) a stretch of primidine bases near the 3' end of intron 1, 2, or 3.

SEQ ID NO: 1 spans the start codon of the IL-10 transcript, and is included here for purposes of comparing the effects of antisense targeting against the AUG start site of the transcript vs a splice-site target region within SEQ ID NO:6.

Also included as antisense compounds of the invention are those targeted to gene transcripts encoding components of the IL-10 signal transduction pathway. The IL-10 receptor alpha (IL10Ra) and suppressor of cytokine signaling 3 (SOCS3) genes encode two such components. These targets are found within the sequences described by the GenBank accession numbers NM_001558 (IL10Ra) and NM_003955 (SOCS3). The SOCS3-AUG start codon and SOCS3 exon 2 splice acceptor (SOCS3 Exon 2SA) targets are defined below in Table 1 as SEQ ID NOs:7 and 8, respectively. The IL10Ra-AUG, exon 2 splice acceptor (IL10Ra Exon 2SA) and exon 6 splice acceptor (IL10Ra Exon 6SA) targets are defined below as SEQ ID NOs:9, 10 and 11, respectively.

TABLE 1

Exemplary Human IL-10 and IL-10 Signal Transduction Target Sequences

| Target | Target Sequence (5' to 3') Gen Bank No. NM 000572 | SEQ ID NO. |
|---|---|---|
| IL10 AUG | CAAGACAGACTTGCAAAAGAAGGCATGCACAGCTCAGCACTGC TCTGTTG (6) | 1 |

TABLE 1-continued

Exemplary Human IL-10 and IL-10 Signal Transduction Target Sequences

| Target | Target Sequence (5' to 3') Gen Bank No. NM 000572 | SEQ ID NO. |
|---|---|---|
| IL10 Exon 2 | CAAATGAAGGATCAGCTGGACAACT | 2 |
| IL10 Exon 2SA | CATTCTCCTTTTGTTCTTCCTGCAG/CAAATGAAGGATCAGCTGGACAACT (7) | 3 |
| IL10 Exon 3SA | ACTCACCTTTGGCTCCTGCCCTTAG/GGTTACCTGGGTTGCCAAGCCTTGT (8) | 4 |
| IL10 Exon 4 | CATCGATTTCTTCCCTGTGAAAACA | 5 |
| IL10 Exon 2-4 | TCATTCTCCTTTTGTTCTTCCTGCAG<u>CAAATGAAGGATCAGCTGGACAACT</u>TGTTGTTAAAGGAGTCCTTGCTGGAGGACTTTAAGGTGAGAGCAGGGGCGGGGTGCTGGGGAGTGTGCAGCATGATTAAGGGAAGGGAGACTCTGCTTCCTGATTGCAGGGAATTGGGTTTGTTTCCTTCGCTTTGAAAAGGAGAAGTGGGAAGATGTTAACTCAGCACATCCAGCAGCCAGAGGGTTTACAAAGGGCTCAGTCCCTTCGGGGAGGCTTCTGGTGAAGGAGGATCGCTAGAACCAAGCTGTCCTCTTAAGCTAGTTGCAGCAGCCCCTCCTCCCAGCCACCTCCGCCAATCTCTCACTCACCTTTGGCTCCTGCCCTTAG<u>GGTTACCTGGGTTGCCAAGCCTTGTCTGAGATGATCCAGTTTTACCTG</u>GAGGAGGTGATGCCCCAAGCTGAGAACCAAGACCCAGACATCAAGGCGCATGTGAACTCCCTGGGGGAGAACCTGAAGACCCTCAGGCTGAGGCTACGGCGCTGTGTAAGTAGCAGATCAGTTTTTTCCCTTGCAGCTGCCCCCAAAATACCATCTCCTACAGACCAGCAGGGACACTCACATCCACAGACACAGCAAAGACACAGACTGGCAGAGCTAGCTGTAAATGAGGAAAGACTCCTGGAGTCAGATCTCTTGCTCATTTCTCTTTGAGCAGGCGTTGGGGGTGGCTGCTAGGCATTACATGTGAAATTTGCAAACAGCTTTCCTGTTATTTGTGAGTCATTTGTGGGTTATTAACTACTCCCCTCTCTCTTCATAAAAGGAGCCCAGAGCTTCAGTCAGGCCTCCACTGCCTCTTTGTAACTAGACCCTGGGCGGGAGCTAAGGTTCCCAAGCAGAGGAAACATCATTCACCTCTTTTAATCTCAATGTTTTGAAAGCAAAGCTCTAAGAAGGGCCCAATTGACTGACAGGATTTCCCCTGGCATTTTAGAAGGGACAAGGGGGCTATTCATCCCCAGGCTAGTGTCTATGAGTAATTCCTCCAGGTAATTTATTTCTCCAACTGAAATGATGCCCTCACTACTAATGGTTTCCCCTGTTCTGTCACCAATATTGGAAAATCAGTTGGTGTCTATTTGTAGGACAAGGCTATGTGAAGGGTTTGGTCCCAGTAGCTTCCCTCCTCAGATGCTTAGAAGTGTTCCTCGGTGGCTGTGACTGACGGGGAGGAACAGGAGAGAGAGGCAGAAAAGGACAGGCTGAAGAATGCCTCGCTCAGCACTGCAGGAGATACTGTAGAGTTCTGGGGGAGGAAGGAATCCCAAGACCTGGGTTGTCATCCAAGCCTTGCAAACATCTTGGAGTGAGTCCTGGAGAAATACATTTAACTCCCAGGGCCATGGAAGCAGGGCTCAGTTCTCTCTGGGAGCTGTGAGGCAAGGCATTTGGATAAATCTGGCCTCCTCATGATGCCACCAGCTTGTCCCCTAAGTGTGATGGACATGCAGCTCGAAGCCAGGATCACCAACACTTTCTCTTTTCTTCCACAGC<u>ATCGATTTCTTCCCTGTGAAAACAAGAGCAAGGCCGTGGAGCAGGTGAAGAATGCCTTTAATAAG</u> | 6 |
| SOCS3 AUG | CAGATCCACGCTGGCTCCGT<u>GCGCCATGGTCACCCACAGCAAG</u>TTTCCCG | 7 |
| SOCS3 Exon 2SA | CGCGCTCGCGCCTTCCTCTCCGCAG | 8 |
| IL10Ra AUG | CCCCGGACGATGCGGCGCGCCC<u>AGGATGCTGCCGTGCCTCGTA</u><u>G</u>TGCTGC | 9 |
| IL10Ra Exon 2SA | GTGGTACTGACACTCTTCTCCCCAG | 10 |
| IL10Ra Exon 6SA | CAAACACATCTCTCTGGGCCTGCAG | 11 |

Human (hu) and murine (mu) IL-10 antisense targeting sequences that are complementary to regions contained within the target sequences listed in Table 1 are shown below in Table 2. As above, the targeting sequence directed to the AUG start codon (SEQ ID NO:7) is included for purposes of experimental comparison with targeting sequences directed against a splice-site target region within SEQ ID NO:6, as will be seen below. The sequences are identified by their corresponding target sequence in Table 1. Thus, SEQ ID NO:13, identified as HuIL-10-SA2 is complementary to the 5'-end 21 bases of exon 2; SEQ ID NO:14 is complementary to the 5'-end 21 bases of exon 3; SEQ ID NO:15, identified as HuIL-10-SD2, is complementary to the 3'-end 22 bases of exon 2; SEQ ID NO:16, identified as HuIL-10-SA4 is complementary to the 5'-end 22 bases of exon 4; SEQ ID NO: 17, identified as MuIL-10-SA4, targets the 5'-end 21 bases of the corresponding exon 4 region of the murine IL-10 transcript; SEQ ID NO: 18, identified as MuIL-10-SA2, targets the 5'-end 21 bases of the corresponding exon 2 region of the murine IL-10 transcript; SEQ ID NO:29, identified as DSscr, is a scrambled (control sequence); and SEQ ID NO:30 is complementary to a target sequence of the human globin gene.

Human and murine IL-10 targeting sequences for IL10Ra and SOCS3 that are complementary to regions contained within the corresponding target sequences listed in Table 1 are also shown below in Table 2 as SEQ ID NOs: 19-28.

TABLE 2

Exemplary Human and Mouse IL-10, IL10RA and SOCS3 Targeting Sequences

| Oligomer | Sequence (5' to 3') | sp. | SEQ ID NO. |
|---|---|---|---|
| HuIL-10-AUG | CAGTGCTGAGCTGTGCATGCC | hu | 12 |
| HuIL-10-SA2 | GTCCAGCTGATCCTTCATTTG | hu | 13 |
| HuIL-10-SA3 | TCATCTCAGACAAGGCTTGGC | hu | 14 |
| HuIL-10-SD2 | CTTAAAGTCCTCCAGCAAGGAC | hu | 15 |
| HuIL-10-SA4 | TTTCACAGGGAAGAAATCGATG | hu | 16 |
| MuIL-10-SA4 | GGAGAAATCGATGCTGAAGAA | mu | 17 |
| MuIL-10-SA2 | GTCCAGCTGGTCCTTTGTGTT | mu | 18 |
| MuIL10Ra-AUG | GCAAACGCGACAACATCCTG | mu | 19 |
| MuIL10Ra-SA2 | AAGGGCTTGGCAGTTCTGTCC | mu | 20 |
| MuIL10Ra-SA6 | TCAGGTTGGTCACAGTGAAAT | mu | 21 |
| MuSOCS3-AUG | TTGCTGTGGGTGACCATGGCG | mu | 22 |
| MuSOCS3-SA2 | GCCGCTACCGCATCCCGGGGA | mu | 23 |
| HuIL10Ra-AUG | CTACGAGGCACGGCAGCATCCTG | hu | 24 |
| HuIL10Ra-SA2 | CGGAGGGCTGGGCAGCTCTGTCC | hu | 25 |
| HuIL10Ra-SA6 | GATGACGTTGGTCACGGTGAAAT | hu | 26 |
| HuSOCS3-AUG | CTTGCTGTGGGTGACCATGGCGC | hu | 27 |
| HuSOCS3-SA2 | GCCGCTACCGCATCCCGGGGGG | hu | 28 |

Additional IL-10 targeting sequence may be selected by first identifying a splice-site target sequence within SEQ ID NO:6, and constructing a targeting sequence complementary to at least 12 contiguous bases, and typically 20 or more bases, of the target sequence. Splice-site target sequences contained within SEQ ID NO:6 can be identified from the exon sequences given above, and for internal intron sequences, through known informatics methods, to identify a branch site (A) in the middle of intron 2 or 3; and a stretch of primidine bases near the 3' end of intron 1, 2, or 3. The same strategy can be utilized for additional IL10Ra and SOCS3 targeting sequences.

Once a targeting sequence has been identified, it can be readily tested for its ability to interfere with normal IL-10 processing, through steps described below. Briefly, a morpholino antisense compound can be prepared according to methods described in Sections B and C below, and the compound can be tested for its ability to block normal IL-10 processing in IL-10 producing cells, e.g., monocyte-derived dendritic cells, in accordance with the in vitro culture methods given in Example 1.

More generally, any type of assay or determination used to measure levels of IL-10 isoforms in culture samples may be employed, such as, but not limited to, immunoassays, including direct competitive, sandwich, direct and indirect cellular, and crisscross enzyme-linked immunosorbent assays (ELISAs), enzyme linked immunosorbent spot (ELISPOT) assays, radioimmunoassays (RIAs), immunoprecipitation, immunohistochemistry, immunofluorescence, immunoblotting, and the like may be employed using polyclonal, monoclonal, polyclonal, and fusion phage antibodies. Simple immunofluorescence using monoclonal and/or fusion phage antibodies are especially preferred in many embodiments. Moreover, the sequence of IL-10 is known so that assessment of mRNA levels by RT-PCR, ribonuclease protection assays, or Northern analysis, are feasible and in many cases preferred.

Alternatively, the antisense compound can be tested for its ability to block normal processing of IL-10, or IL10Ra and SOCS3, by direct screening of the compound in a test animal, e.g., murine model, where the sequence tested is targeted against a selected splice site target sequence of the corresponding animal (mice) IL-10 pre-processed transcript sequence. In this approach, the test agent is administered to the experimental animal, a biological sample is taken from the animal and from a control animal of the same species, and the mRNA concentration of the spliced products are measured. The cellular and cytoplasmic levels of IL-10 in both samples are measured. The levels in the control and experimental animals are compared and test agents useful in promoting immunologic activation are identified by observation of increased levels of the specific IL-10 alternatively spliced mRNA isoform in the test animal sample over the IL-10 levels in the control animal sample. As mentioned above, any type of biological sample of material that contains or expresses IL-10 may be employed, such as, but not limited to, cells, blood, plasma, serum, lymph nodes, splenocytes, tissues, and the like may be employed. Samples comprising T-lymphocytes are preferred in many embodiments.

B. Constructing the Antisense Oligonucleotide

Figure 1B:
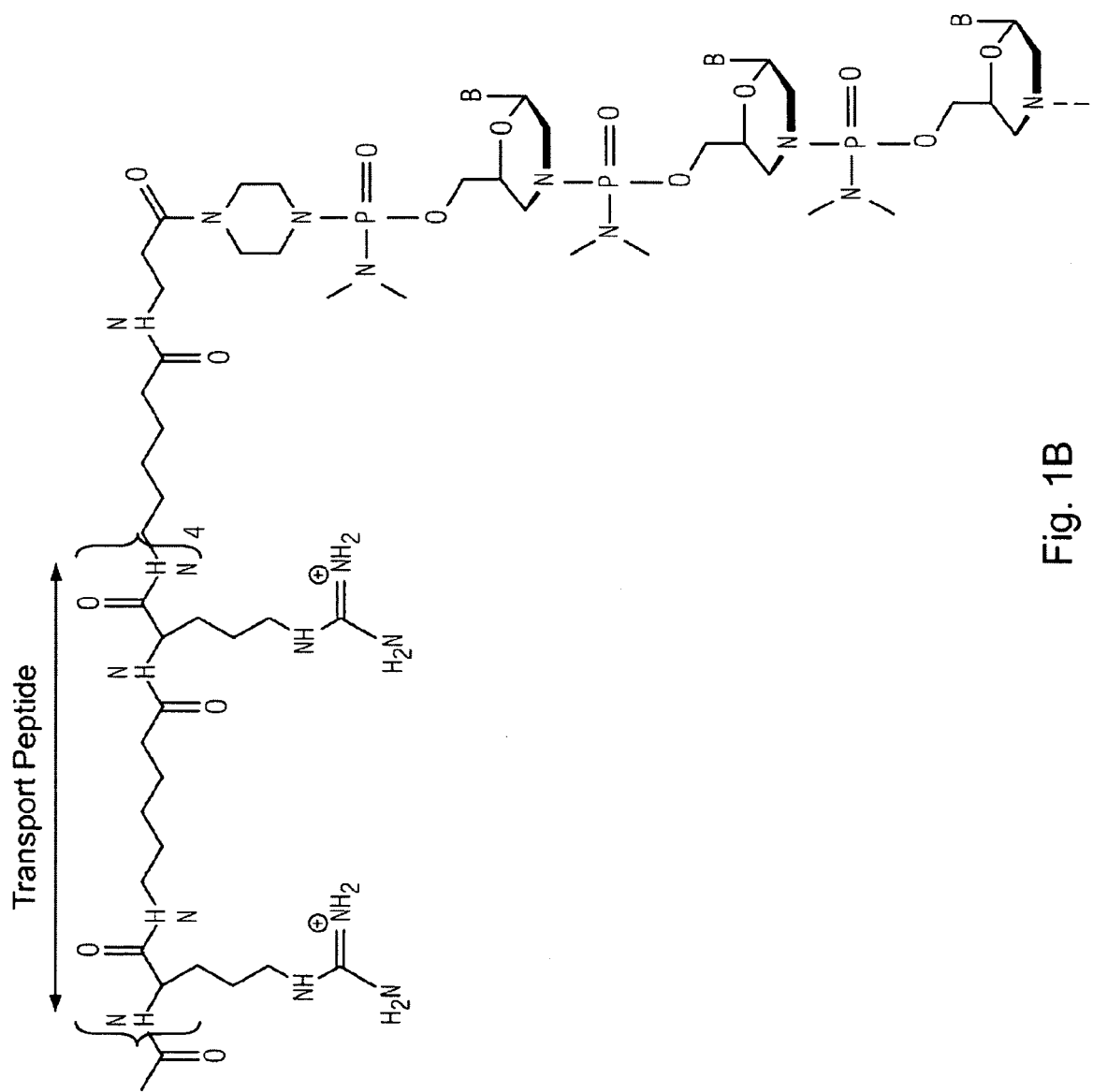
Figure 1C:
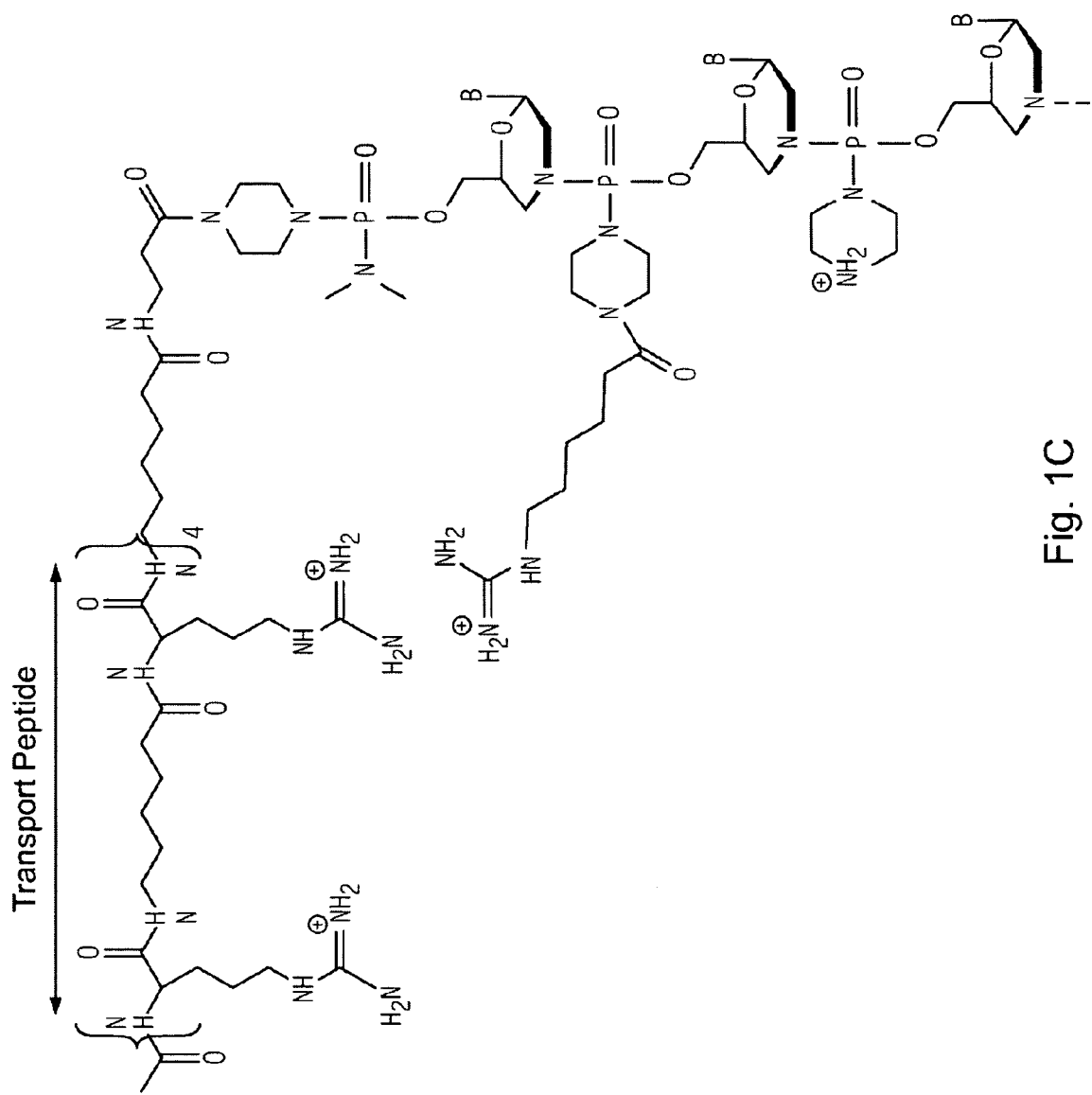

Examples of morpholino oligonucleotides having phosphorus-containing backbone linkages are illustrated in FIGS. 1A-1C. Especially preferred is a phosphorodiamidate-linked morpholino oligonucleotide such as shown in FIG. 1B, which is modified, in accordance with one aspect of the present invention, to contain positively charged groups at preferably 10%-50% of its backbone linkages. Morpholino oligonucleotides with uncharged backbone linkages, including antisense oligonucleotides, are detailed, for example, in (Summerton and Weller 1997) and in co-owned U.S. Pat. Nos. 5,698,685, 5,217,866, 5,142,047, 5,034,506, 5,166,315, 5,185,444, 5,521,063, and 5,506,337, all of which are expressly incorporated by reference herein.

Important properties of the morpholino-based subunits include: 1) the ability to be linked in a oligomeric form by stable, uncharged or positively charged backbone linkages; 2) the ability to support a nucleotide base (e.g. adenine, cytosine, guanine, thymidine, uracil and inosine) such that the polymer formed can hybridize with a complementary-base target nucleic acid, including target RNA, Tm values above about 45° C. in relatively short oligonucleotides (e.g., 10-15 bases); 3) the ability of the oligonucleotide to be actively or passively transported into mammalian cells; and 4) the ability of the antisense oligonucleotide:RNA heteroduplex to resist RNAse and RNaseH degradation, respectively.

Figure 1D:
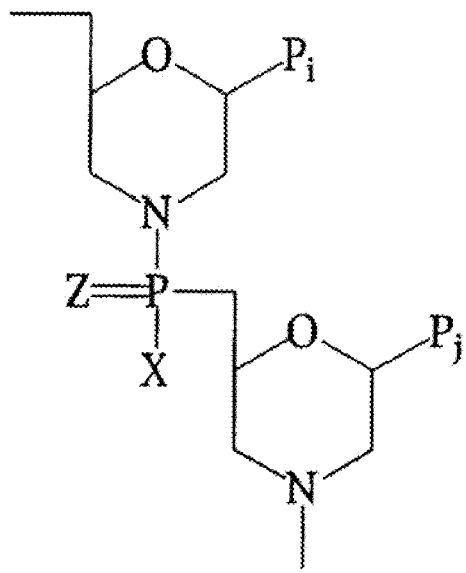
FIGS. 1D-G show the repeating subunit segment of exemplary morpholino oligonucleotides, designated D through G.
Figure 1E:
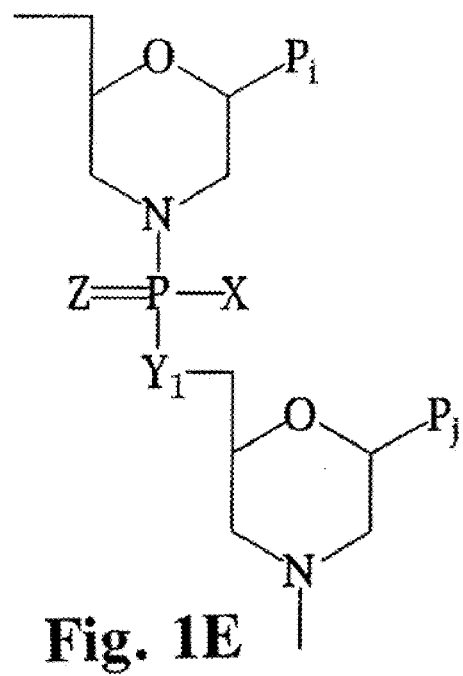

Exemplary backbone structures for antisense oligonucleotides of the claimed subject matter include the morpholino subunit types shown in FIGS. 1D-G, each linked by an uncharged or positively charged, phosphorus-containing subunit linkage. FIG. 1D shows a phosphorus-containing linkage which forms the five atom repeating-unit backbone, where the morpholino rings are linked by a 1-atom phosphoamide linkage. FIG. 1E shows a linkage which produces a 6-atom repeating-unit backbone. In this structure, the atom Y linking the 5' morpholino carbon to the phosphorus group may be sulfur, nitrogen, carbon or, preferably, oxygen. The X moiety pendant from the phosphorus may be fluorine, an alkyl or substituted alkyl, an alkoxy or substituted alkoxy, a thioalkoxy or substituted thioalkoxy, or unsubstituted, monosubstituted, or disubstituted nitrogen, including cyclic structures, such as morpholines or piperidines. Alkyl, alkoxy and thioalkoxy preferably include 1-6 carbon atoms. The Z moieties are sulfur or oxygen, and are preferably oxygen.

Figure 1F:
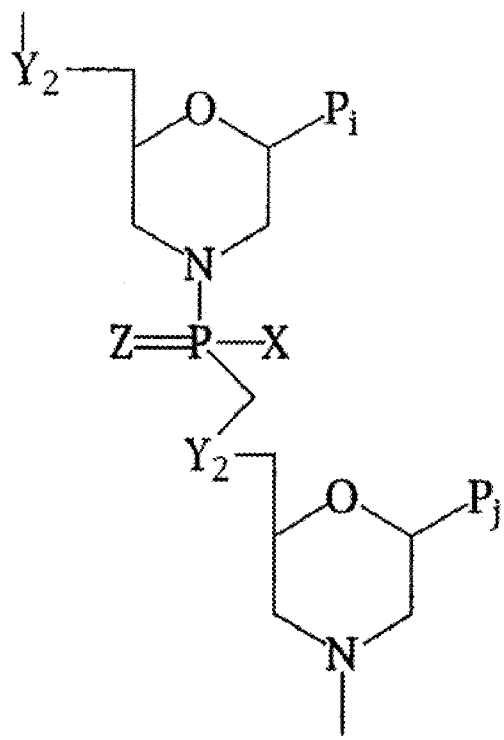
Figure 1G:
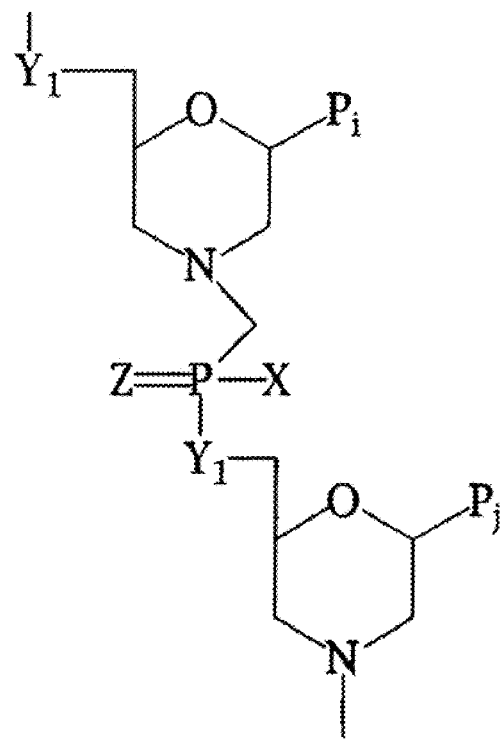

The linkages shown in FIGS. 1F and 1G are designed for 7-atom unit-length backbones. In structure 1F, the X moiety is as in Structure 1E, and the Y moiety may be methylene, sulfur, or, preferably, oxygen. In Structure 1G, the X and Y moieties are as in Structure 1E. Particularly preferred morpholino oligonucleotides include those composed of morpholino subunit structures of the form shown in FIG. 1E, where X=NH$_2$, N(CH$_3$)$_2$, or 1-piperazine or other charged group, Y=O, and Z=O.

As noted above, the substantially uncharged oligonucleotide may be modified, in accordance with an aspect of the invention, to include charged linkages, e.g. up to about 1 per every 2-5 uncharged linkages, such as about 4-5 per every 10 uncharged linkages. Optimal improvement in antisense activity may be seen when about 25% of the backbone linkages are cationic. Suboptimal enhancement is typically seen with a small number e.g., 10-20% cationic linkages, and where the number of cationic linkages are in the range 50-80%, and typically above about 60%, the sequence specificity of the antisense binding to its target may be compromised or lost.

Additional experiments conducted in support of the present invention indicate that the enhancement seen with added cationic backbone charges may, in some cases, be further enhanced by distributing the bulk of the charges close of the "center-region" backbone linkages of the antisense oligonucleotide, e.g., in a 20mer oligonucleotide with 8 cationic backbone linkages, having at least 70% of these charged linkages localized in the 10 centermost linkages.

The antisense compounds can be prepared by stepwise solid-phase synthesis, employing methods detailed in the references cited above, and below with respect to the synthesis of oligonucleotides having a mixture or uncharged and cationic backbone linkages. In some cases, it may be desirable to add additional chemical moieties to the antisense compound, e.g. to enhance pharmacokinetics or to facilitate capture or detection of the compound. Such a moiety may be covalently attached, typically to a terminus of the oligomer, according to standard synthetic methods. For example, addition of a polyethyleneglycol moiety or other hydrophilic polymer, e.g., one having 10-100 monomeric subunits, may be useful in enhancing solubility. One or more charged groups, e.g., anionic charged groups such as an organic acid, may enhance cell uptake. A reporter moiety, such as fluorescein or a radiolabeled group, may be attached for purposes of detection. Alternatively, the reporter label attached to the oligomer may be a ligand, such as an antigen or biotin, capable of binding a labeled antibody or streptavidin. In selecting a moiety for attachment or modification of an antisense compound, it is generally of course desirable to select chemical compounds of groups that are biocompatible and likely to be tolerated by a subject without undesirable side effects.

As noted above, the antisense compound can be constructed to contain a selected number of cationic linkages interspersed with uncharged linkages of the type described above. The intersubunit linkages, both uncharged and cationic, preferably are phosphorus-containing linkages, having the structure:

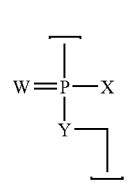

where
W is S or O, and is preferably O,
X=NR$^1$R$^2$ or OR$^6$,
Y=O or NR$^7$,
and each said linkage in the oligomer is selected from:
(a) uncharged linkage (a), where each of R$^1$, R$^2$, R$^6$ and R$^7$ is independently selected from hydrogen and lower alkyl;
(b1) cationic linkage (b1), where X=NR$^1$R$^2$ and Y=O, and NR$^1$R$^2$ represents an optionally substituted piperazino group, such that R$^1$R$^2$=—CHRCHRN(R$^3$)(R$^4$)CHRCHR—, where
each R is independently H or CH$_3$,
R$^4$ is H, CH$_3$, or an electron pair, and
R$^3$ is selected from H, lower alkyl, e.g. CH$_3$, C(=NH)NH$_2$, Z-L-NHC(=NH)NH$_2$, and [C(O)CHR'NH]$_m$H, where: Z is C(O) or a direct bond, L is an optional linker up to 18 atoms in length, preferably up to 12 atoms, and more preferably up to 8 atoms in length, having bonds selected from alkyl, alkoxy, and alkylamino, R' is a side chain of a naturally occurring amino acid or a one- or two-carbon homolog thereof, and m is 1 to 6, preferably 1 to 4;
(b2) cationic linkage (b2), where X=NR$^1$R$^2$ and Y=O, R$^1$=H or CH$_3$, and R$^2$=LNR$^3$R$^4$R$^5$, where L, R$^3$, and R$^4$ are as defined above, and R$^5$ is H, lower alkyl, or lower (alkoxy) alkyl; and
(b3) cationic linkage (b3), where Y=NR$^7$ and X=OR$^6$, and R$^7$=LNR$^3$R$^4$R$^5$, where L, R$^3$, R$^4$ and R$^5$ are as defined above, and R$^6$ is H or lower alkyl; and at least one said linkage is selected from cationic linkages (b1), (b2), and (b3).

Preferably, the oligomer includes at least two consecutive linkages of type (a) (i.e. uncharged linkages). In further embodiments, at least 5% of the linkages in the oligomer are cationic linkages (i.e. type (b1), (b2), or (b3)); for example, 10% to 60%, and preferably 20-50% linkages may be cationic linkages.

In one embodiment, at least one linkage is of type (b1), where, preferably, each R is H, R$^4$ is H, CH$_3$, or an electron pair, and R$^3$ is selected from H, lower alkyl, e.g. CH$_3$, C(=NH)NH$_2$, and C(O)-L-NHC(=NH)NH$_2$. The latter two embodiments of R$^3$ provide a guanidino moiety, either attached directly to the piperazine ring, or pendant to a linker group L, respectively. For ease of synthesis, the variable Z in R$^3$ is preferably C(O) (carbonyl), as shown.

The linker group L, as noted above, contains bonds in its backbone selected from alkyl (e.g. —CH$_2$—CH$_2$—), alkoxy (—C—O—), and alkylamino (e.g. —CH$_2$—NH—), with the proviso that the terminal atoms in L (e.g., those adjacent to carbonyl or nitrogen) are carbon atoms. Although branched linkages (e.g. —CH$_2$—CHCH$_3$—) are possible, the linker is preferably unbranched. In one embodiment, the linker is a hydrocarbon linker. Such a linker may have the structure —$(CH_2)_n$—, where n is 1-12, preferably 2-8, and more preferably 2-6.

The morpholino subunits have the structure:

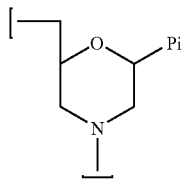
(i)

where Pi is a base-pairing moiety, and the linkages depicted above connect the nitrogen atom of (i) to the 5' carbon of an adjacent subunit. The base-pairing moieties Pi may be the same or different, and are generally designed to provide a sequence which binds to a target nucleic acid.

The use of embodiments of linkage types (b1), (b2) and (b3) above to link morpholino subunits may be illustrated graphically as follows:

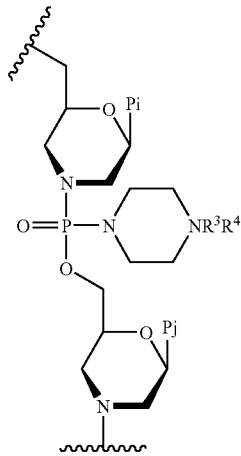
(b1)

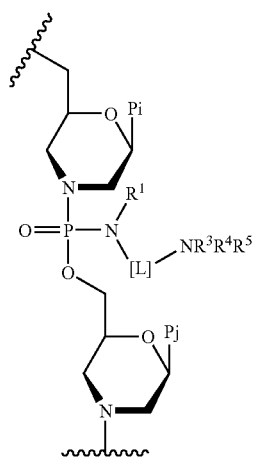
(b2)

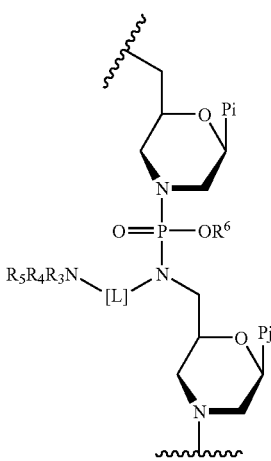
(b3)

Preferably, all cationic linkages in the oligomer are of the same type; i.e. all of type (b1), all of type (b2), or all of type (b3).

In further embodiments, the cationic linkages are selected from linkages (b1') and (b1") as shown below, where (b1") is referred to herein as a "Pip" linkage and (b1") is referred to herein as a "GuX" linkage:

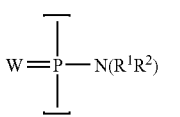
(a)

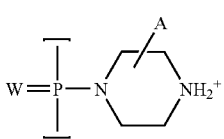
(b1')

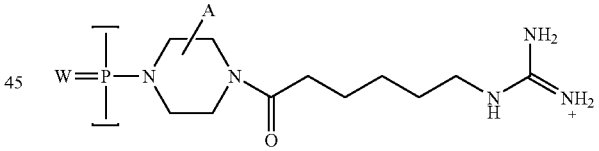
(b1")

In the structures above, W is S or O, and is preferably O; each of $R^1$ and $R^2$ is independently selected from hydrogen and lower alkyl, and is preferably methyl; and A represents hydrogen or a non-interfering substituent on one or more carbon atoms in (b1') and (b1"). Preferably, the ring carbons in the piperazine ring are unsubstituted; however, they may include non-interfering substituents, such as methyl or fluorine. Preferably, at most one or two carbon atoms is so substituted.

In further embodiments, at least 10% of the linkages are of type (b1') or (b1"); for example, 10%-60% and preferably 20% to 50%, of the linkages may be of type (b1') or (b1").

In other embodiments, the oligomer contains no linkages of the type (b1') above. Alternatively, the oligomer contains no linkages of type (b1) where each R is H, $R^3$ is H or $CH_3$, and $R^4$ is H, $CH_3$, or an electron pair.

The morpholino subunits may also be linked by non-phosphorus-based intersubunit linkages, as described further below, where at least one linkage is modified with a pendant cationic group as described above.

Other oligonucleotide analog linkages which are uncharged in their unmodified state but which could also bear a pendant amine substituent could be used. For example, a 5'nitrogen atom on a morpholino ring could be employed in a sulfamide linkage or a urea linkage (where phosphorus is replaced with carbon or sulfur, respectively) and modified in a manner analogous to the 5'-nitrogen atom in structure (b3) above.

Oligomers having any number of cationic linkages are provided, including fully cationic-linked oligomers. Preferably, however, the oligomers are partially charged, having, for example, 10%-80%. In preferred embodiments, about 10% to 60%, and preferably 20% to 50% of the linkages are cationic.

In one embodiment, the cationic linkages are interspersed along the backbone. The partially charged oligomers preferably contain at least two consecutive uncharged linkages; that is, the oligomer preferably does not have a strictly alternating pattern along its entire length.

Also considered are oligomers having blocks of cationic linkages and blocks of uncharged linkages; for example, a central block of uncharged linkages may be flanked by blocks of cationic linkages, or vice versa. In one embodiment, the oligomer has approximately equal-length 5', 3' and center regions, and the percentage of cationic linkages in the center region is greater than about 50%, preferably greater than about 70%.

Oligomers for use in antisense applications generally range in length from about 10 to about 40 subunits, more preferably about 10 to 30 subunits, and typically 15-25 bases. For example, an oligomer of the invention having 19-20 subunits, a useful length for an antisense compound, may ideally have two to ten, e.g. four to eight, cationic linkages, and the remainder uncharged linkages. An oligomer having 14-15 subunits may ideally have two to five, e.g. 3 or 7, cationic linkages and the remainder uncharged linkages.

Each morpholino ring structure supports a base pairing moiety, to form a sequence of base pairing moieties which is typically designed to hybridize to a selected antisense target in a cell or in a subject being treated. The base pairing moiety may be a purine or pyrimidine found in native DNA or RNA (A, G, C, T, or U) or an analog, such as hypoxanthine (the base component of the nucleoside inosine) or 5-methyl cytosine.

C. Peptide Transporters

The antisense compounds of the invention may include an oligonucleotide moiety conjugated to an arginine-rich peptide transport moiety effective to enhance transport of the compound into cells. The transport moiety is preferably attached to a terminus of the oligomer, as shown, for example, in FIGS. 1B and 1C. The peptide transport moiety preferably comprises 6 to 16 subunits selected from X' subunits, Y' subunits, and Z' subunits, where (a) each X' subunit independently represents lysine, arginine or an arginine analog, said analog being a cationic α-amino acid comprising a side chain of the structure $R^1N=C(NH_2)R^2$, where $R^1$ is H or R; $R^2$ is R, $NH_2$, NHR, or $NR_2$, where R is lower alkyl or lower alkenyl and may further include oxygen or nitrogen; $R^1$ and $R^2$ may together form a ring; and the side chain is linked to said amino acid via $R^1$ or $R^2$;

(b) each Y' subunit independently represents a neutral amino acid $-C(O)-(CHR)_n-NH-$, where n is 2 to 7 and each R is independently H or methyl; and (c) each Z' subunit independently represents an α-amino acid having a neutral aralkyl side chain;

wherein the peptide comprises a sequence represented by one of $(X'Y'X')_p$, $(X'Y')_m$, and $(X'Z'Z')_p$, where p is 2 to 5 and m is 2 to 8.

In selected embodiments, for each X', the side chain moiety is guanidyl, as in the amino acid subunit arginine (Arg). In further embodiments, each Y' is $-CO-(CH_2)_n CHR-NH-$, where n is 2 to 7 and R is H. For example, when n is 5 and R is H, Y' is a 6-aminohexanoic acid subunit, abbreviated herein as Ahx; when n is 2 and R is H, Y' is a β-alanine subunit, abbreviated herein as B.

Preferred peptides of this type include those comprising arginine dimers alternating with single Y' subunits, where Y' is preferably Ahx. Examples include peptides having the formula $(RY'R)_p$ or the formula $(RRY')_p$, where Y' is preferably Ahx. In one embodiment, Y' is a 6-aminohexanoic acid subunit, R is arginine and p is 4.

In a further embodiment, each Z' is phenylalanine, and m is 3 or 4.

The conjugated peptide is preferably linked to a terminus of the oligomer via a linker Ahx-B, where Ahx is a 6-aminohexanoic acid subunit and B is a β-alanine subunit, as shown, for example, in FIGS. 1B and 1C.

In selected embodiments, for each X', the side chain moiety is independently selected from the group consisting of guanidyl ($HN=C(NH_2)NH-$), amidinyl ($HN=C(NH_2)C<$), 2-aminodihydropyrimidyl, 2-aminotetrahydropyrimidyl, 2-aminopyridinyl, and 2-aminopyrimidonyl, and it is preferably selected from guanidyl and amidinyl. In one embodiment, the side chain moiety is guanidyl, as in the amino acid subunit arginine (Arg).

The Y' subunits are either contiguous, in that no X' subunits intervene between Y' subunits, or interspersed singly between X' subunits. However, the linking subunit may be between Y' subunits. In one embodiment, the Y' subunits are at a terminus of the transporter; in other embodiments, they are flanked by X' subunits. In further preferred embodiments, each Y' is $-CO-(CH_2)_n-CHR-NH-$, where n is 2 to 7 and R is H. For example, when n is 5 and R is H, Y' is a 6-aminohexanoic acid subunit, abbreviated herein as Ahx. In selected embodiments of this group, each X' comprises a guanidyl side chain moiety, as in an arginine subunit. Preferred peptides of this type include those comprising arginine dimers alternating with single Y' subunits, where Y' is preferably Ahx. Examples include peptides having the formula $(RY'R)_4$ or the formula $(RRY')_4$ where Y' is preferably Ahx. In the latter case, the nucleic acid analog is preferably linked to a terminal Y' subunit, preferably at the C-terminus, as shown, for example, in FIGS. 1B and 1C. The preferred linker is of the structure AhxB, where Ahx is a 6-aminohexanoic acid subunit and B is a β-alanine subunit.

The transport moieties as described above have been shown to greatly enhance cell entry of attached oligomers, relative to uptake of the oligomer in the absence of the attached transport moiety, and relative to uptake by an attached transport moiety lacking the hydrophobic subunits Y'. Such enhanced uptake is preferably evidenced by at least a two-fold increase, and preferably a four-fold increase, in the uptake of the compound into mammalian cells relative to uptake of the agent by an attached transport moiety lacking the hydrophobic subunits Y'. Uptake is preferably enhanced at least twenty fold, and more preferably forty fold, relative to the unconjugated compound.

A further benefit of the transport moiety is its expected ability to stabilize a duplex between an antisense compound and its target nucleic acid sequence, presumably by virtue of electrostatic interaction between the positively charged transport moiety and the negatively charged nucleic acid. The number of charged subunits in the transporter is less than 14, as noted above, and preferably between 8 and 11, since too high a number of charged subunits may lead to a reduction in sequence specificity.

The use of arginine-rich peptide transporters (i.e., cell-penetrating peptides) are particularly useful in practicing the present invention. Certain peptide transporters have been shown to be highly effective at delivery of antisense compounds into primary leukocytes (Marshall, Oda et al. 2007). Furthermore, compared to other known peptide transporters such as Penetratin, the peptide transporters described herein, when conjugated to an antisense PMO, demonstrate an enhanced ability to alter splicing of several gene transcripts (Marshall, Oda et al. 2007). Especially preferred are the P007 and CPO6062 transport peptides listed below in Table 3 (SEQ ID NOS:36 and 40, respectively).

Exemplary peptide transporters, including linkers (B or AhxB) are given below in Table 3. Preferred sequences are those designated P007 (SEQ ID NO:36) and CPO6020 (SEQ ID NO:40).

TABLE 3

Exemplary Peptide Transporters for Intracellular Delivery of PMO

| Peptide | Sequence (N-terminal to C-terminal) | SEQ ID NO: |
|---|---|---|
| (RRAhx)$_4$B | RRAhxRRAhxRRAhxRRAhxB | 35 |
| (RAhxR)$_4$AhxB (P007) | RAhxRRAhxRRAhxRRAhxRAhxB | 36 |
| (AhxRR)$_4$AhxB | AhxRRAhxRRAhxRRAhxRRAhxB | 37 |
| (RAhx)$_6$B | RAhxRAhxRAhxRAhxRAhxRAhxB | 38 |
| (RAhx)$_8$B | RAhxRAhxRAhxRAhxRAhxRAhxRAhxRAhxB | 39 |
| (RAhxR)$_3$AhxB | RAhxRRAhxRRAhxR AhxB | 40 |
| (RAhxRRBR)$_2$AhxB (CPO6062) | RAhxRRBRRAhxRRBRAhxB | 41 |
| ((RB)3RAhx)$_2$B | RBRBRBRAhxRBRBRBRAhxB | 42 |

III. Methods of Treatment

In one aspect, the invention is directed to methods of inducing and enhanced immunological response in vivo in a patient, by administering to the patient a therapeutically effective amount of the IL-10 antisense compound of the invention, as described herein.

A. Treatment of Pathogenic Infection

In one embodiment, the treatment method of the invention is aimed at treatment a mammalian subject, e.g., human subject, diagnosed with an infection, e.g., viral or bacterial infection, or disease-causing protozoan parasite such as *Plasmodium* in malaria. In particular, the infectious pathogen is one capable of inhibiting the body's immune response to the pathogen by up-regulation of IL-10 in certain of the body's immune cells, including macrophages, monocytes and dendritic cells. The enhanced level of IL-10 production in the body may be assessed, for example, by measuring the level of IL-10 in a blood or serum sample, and comparing the measured levels against known normal levels in non-infected individuals. Methods for measuring IL-10 in a body fluid sample using antibody detection are well known. However, the patient may also be treated prophylactically with the antisense compound, immediately after contact with the infectious agent, or in anticipation of contact with the infectious agent, in which case, administration of the compound is carried out in the absence of a measured level of IL10 up-regulation.

In the usual case, the infected subject is in need of enhanced T cell immunity in response to a chronic disease or infection. In this embodiment, administration of the IL-10 antisense compound will result in activation of CD8+ T cells. Typically, the patient is treated with the antisense compound in peptide conjugate form, and the compound is given periodically, e.g., once every 3-14 days, until immunological enhancement is established. Immunological enhancement can be monitored during treatment by testing patient T cells for reactivity with disease-specific MHC antigens in a standard in vitro test, as detailed below.

For the treatment of a chronic disorder, such as a chronic viral infection or cancer, the patient is given an initial single dose of the IL-10 antisense conjugate, then additional doses on a periodic basis, e.g., every 3-14 days, until improvement in the disorder is observed. As above, development of immunological enhancement can be monitored during treatment by testing T cells from a blood sample for their ability to react with a selected, relevant antigen in vitro.

It will be understood that in vivo administration of such an IL-10 antisense compound is dependent upon, (1) the duration, dose and frequency of antisense administration, and (2) the general condition of the subject. A suitable dose can be approximated from animal model studies and extrapolated to patient weight. Typically, one or more doses of IL-10 antisense compound are administered, generally at regular intervals for a period of about one to two weeks. Preferred doses for oral administration are from about 5 mg oligomer/patient to about 1000 mg oligomer/patient (based on an adult weight of 70 kg). In some cases, doses of greater than 1000 mg oligomer/patient may be necessary. For parenteral administration, including intravenous, the preferred doses are from about 5 mg oligomer/patient to about 1000 mg oligomer/patient (based on an adult weight of 70 kg).

The antisense agent is generally administered in an amount sufficient to result in a peak blood concentration of at least 200-400 nM antisense compound.

In general, the method comprises administering to a subject, in a suitable pharmaceutical carrier, an amount of an IL-10 morpholino antisense compound effective to alter expression of full-length IL-10 mRNA or expression of functional IL-10.

Effective delivery of an antisense compound to the target nucleic acid is an important aspect of the methods described herein. In accordance with the invention, such routes of antisense compound delivery include, but are not limited to, inhalation; transdermal delivery; various systemic routes, including oral and parenteral routes, e.g., intravenous, subcutaneous, intraperitoneal, or intramuscular delivery, as detailed further below. It is appreciated that any methods which are effective to deliver an anti-IL-10 PMO into the bloodstream are also contemplated.

In preferred applications of the method, the subject is a human subject and the methods of the invention are applicable to treatment of any condition wherein either promoting immunological tolerance or enhancing immune activation would be effective to result in an improved therapeutic outcome for the subject under treatment.

It will be understood that an effective in vivo treatment regimen using an IL-10 PMO antisense compound of the invention will vary according to the frequency and route of administration as well as the condition of the subject under treatment. Accordingly, such in vivo therapy will generally require monitoring by tests appropriate to the condition being treated and a corresponding adjustment in the dose or treatment regimen in order to achieve an optimal therapeutic outcome.

In a typical treatment method, the subject, e.g., human patient, is also treated with one or more compounds designed to target the infectious pathogen, such as an anti-viral or anti-bacterial agent. The antisense compound and anti-pathogen compound may be formulated as a single composition, but more typically are administered as separate agents, where the anti-pathogen agent is administered according to established doses and dosing schedules. For treating a variety of viral infections, the anti-viral compound may itself be an antisense compound that inhibits viral replication by targeting the viral genome.

B. Treatment of Cancer

In another embodiment, the treatment method of the invention is aimed at treating a cancer in a mammalian subject, e.g., human subject. The cancer is one capable of inhibiting the body's immune response to cancer cells by up-regulation of IL-10 in certain of the body's immune cells, including macrophages, monocytes and dendritic cells. The enhanced level of IL-10 production in the body may be assessed, for example, by measuring the level of IL-10 in a blood or serum sample, and comparing the measured levels against known normal levels in non-infected individuals, or by measuring the level of IL-10 in the extracellular environment of the cancer, e.g., tumor. Typically, the patient is treated with the antisense compound in peptide conjugate form.

For the treatment of cancer, the patient is given an initial single dose of the IL-10 antisense compound, then additional doses are administered on a periodic basis, e.g., every 3-14 days, during the course of the cancer treatment. As above, development of immunological enhancement can be monitored during treatment by testing T cells from a blood sample for their ability to react with a selected, relevant antigen in vitro.

Dose amounts and schedules, and routes of administration are similar to those described in Section 111A above. In addition, the antisense compound may be administered directly into a tumor, or in the region of the tumor, to localize the agent at the target site. Alternatively, the antisense compound can be administered in carriers, such as liposomes, that are known to localize by vascular extravasation at tumor sites.

In a typical treatment method, the subject, e.g., human patient, is also treated with one or more anti-neoplastic agents designed to target the cancer, such as anti-cancer compounds or radiation treatment. The antisense compound and anti-cancer compound may be formulated as a single composition, but more typically are administered as separate agents, where the anti-cancer agent is administered according to established doses and dosing schedules.

C. Administration of IL-10 Antisense Compounds

Transdermal delivery of an antisense compound may be accomplished by use of a pharmaceutically acceptable carrier. One example of morpholino oligomer delivery is described in PCT patent application WO97/40854, incorporated herein by reference.

In one preferred embodiment, the antisense compound is contained in a pharmaceutically acceptable carrier, and delivered orally. In a further aspect of this embodiment, the antisense compound is administered at regular intervals for a short time period, e.g., daily for two weeks or less. However, in some cases the antisense compound is administered intermittently over a longer period of time.

It follows that a morpholino antisense oligonucleotide composition may be administered in any convenient vehicle, which is physiologically acceptable. Such an oligonucleotide composition may include any of a variety of standard pharmaceutically accepted carriers employed by those of ordinary skill in the art. Examples of such pharmaceutical carriers include, but are not limited to, saline, phosphate buffered saline (PBS), water, aqueous ethanol, emulsions such as oil/water emulsions, triglyceride emulsions, wetting agents, tablets and capsules. It will be understood that the choice of suitable physiologically acceptable carrier will vary dependent upon the chosen mode of administration.

In some instances liposomes may be employed to facilitate uptake of an antisense oligonucleotide into cells. Hydrogels may also be used as vehicles for antisense compound administration, for example, as described in WO 93/01286. Alternatively, an oligonucleotide may be administered in microspheres or microparticles.

Sustained release compositions are also contemplated within the scope of this application. These may include semipermeable polymeric matrices in the form of shaped articles such as films or microcapsules.

D. Monitoring Treatment

The efficacy of a given therapeutic regimen involving the methods described herein, may be monitored, e.g., by conventional FACS assays for the phenotype of cells in the circulation of the subject under treatment or cells in culture. Such analysis is useful to monitor changes in the numbers of cells of various lineages, in particular, activated T and B cells in response to a specific antigen or pathogen.

Phenotypic analysis is generally carried out using monoclonal antibodies specific to the cell type being analyzed. The use of monoclonal antibodies in such phenotypic analyses is routinely employed by those of skill in the art for cellular analyses and monoclonal antibodies specific to particular cell types are commercially available. Alternatively, efficacy can be monitored using a variety of techniques including isolation of CD8+ T cells from a treated patient followed by antigen-specific tetramer staining and detection by flow cytometry, antigen-specific ELISPOT assays for TNF-alpha and gamma interferon, or chromium release from antigen expressing cells incubated in the presence of a patient's CD8+ T-cells. An indirect assessment of enhanced cellular immunity is an improved clinical status of the patient. The anti-IL-10 PMO treatment regimen may be adjusted (dose, frequency, route, etc.), as indicated, based on the results of the phenotypic and biological assays described above.

IV. Vaccine Composition

Many vaccines would be enhanced if a stronger and more durable immune response could be elicited. Traditional adjuvants have no antigen-specific properties and range from mineral salts to oil-based emulsions such as incomplete Freund's adjuvant (IFA). Molecular adjuvants are defined as any of a number of macromolecules that interact with antigen presenting cells (APCs) along with the antigen to elicit an improvement in the quality of the ensuing immune response (Kornbluth and Stone 2006). IL-10 ablation can act as a molecular adjuvant since reduction of IL-10-mediated immunosuppression could prove advantageous in many if not most vaccination strategies.

In a typical vaccination method, in accordance with the invention, the antisense compound of the invention is administered to a subject, e.g., human subject, in an amount of between about 1 to 30 mg/kg of a antisense conjugate in combination with the vaccine. The route of administration may be intravenous (i.v.), subcutaneous (s.q.), or intramuscular (i.m.) and PPMO treatment is anticipated to be beneficial if administered prior to, simultaneously with and/or following vaccine administration. A benefit may be realized if the route of administration of the antisense compound matches that of the vaccine. Multiple PPMO treatments are anticipated as being beneficial to the vaccination strategy but a single PPMO treatment may be sufficient to provide a significant benefit.

In a related aspect, the invention includes a vaccine against a pathogen or tumor. The composition is formulated to include an antigenic component capable of eliciting an immune response against the pathogen or tumor, an antisense oligonucleotide compound of the invention, and an adjuvant in which the antigenic component and antisense compound are formulated. Any available vaccine may be used in formulating the vaccine of the invention, including conventional vaccine employed for providing immunity against a variety of infectious conditions. To the existing vaccine, which contains one or more antigens of interest in a conventional adjuvant, the antisense compound, e.g., conjugate compound, is added in an amount sufficient to provide an affective dose of the compound with the recommended vaccine dose. For a parenterally administered vaccine, a preferred dose of the compound is between about 5 mg oligomer/patient to about 1000 mg oligomer/patient (based on an adult weight of 70 kg).

The vaccine composition of the invention can find use as therapeutic vaccines against numerous pathogens including, but not limited to, cancer (Banchereau and Palucka 2005), HIV infection (Van Gulck, Ponsaerts et al. 2006), HCV infection (Encke, Findeklee et al. 2005) and *Chlamydia* infection (Igietseme, Ananaba et al. 2000).

In still another aspect, the antisense composition may be used to enhance the immune response in DC-based (dendritic-cell-based) vaccines. In a typical use of the present invention to enhance a DC vaccine, monocyte derived dendritic cells are isolated from a patient's peripheral blood mononuclear cells (PBMCs) as described (Romani, Gruner et al. 1994) and treated ex vivo with the anti-IL-10 PPMO of the present invention The DC are loaded with the desired antigen and then treated with the antisense compound at a concentration of between 1 to 10 micromolar, preferably between 3 and 5 micromolar, for 12-24 hours prior to reintroduction into the patient. Enhanced cellular immunity can be assessed using a variety of techniques including isolation of CD8+ T cells from a treated patient followed by antigen-specific tetramer staining and detection by flow cytometry, antigen-specific ELISPOT assays for TNF-alpha and gamma interferon, or chromium release from antigen expressing cells incubated in the presence of a patient's CD8+ T-cells. An indirect assessment of enhanced cellular immunity is an improved clinical status of the patient.

Using a variety of antisense compounds and methods of the invention, modulation of IL-10 expression in antigen presenting cells and activation of antigen specific Th1 cells provides a benefit for adoptive immunotherapy vaccination strategies against a number of pathogens and tumors. Specifically, ex vivo inhibition of functional IL-10 expression by antigen-pulsed dendritic cells (DC) fosters antigen presentation and enhanced Th1 activation. DC-based cellular vaccines have numerous advantages for a variety of clinical applications. First, DC can process either intact antigens (e.g, whole viruses), components of an antigen (e.g., proteins) or peptide fragments of an antigen and select the appropriate immunodominant epitopes for presentation and activation of specific Th1 cells. This inherent ability of DC obviates the need for identifying the most immunoprotective antigens and immunogenic epitopes. Second, efficient ex vivo propagation of DC from peripheral blood of humans has proven beneficial in clinical applications of DC in immunotherapies. Finally, IL-10-suppressed DC-based vaccination should induce a high frequency of antigen-specific Th1 cells and long term protective immunity.

From the foregoing, it will be appreciated how various objects and features of the invention are met. The activation of antigen specific T cells capable of clearing a chronic infection or disease is an important therapy for numerous human diseases where immunological activation is beneficial. The present invention provides a method of specifically enhancing the activation of these cells through the use of antisense compounds designed to inhibit IL-10 expression during the stage of antigen-specific T-cell activation thereby preventing the generation of anergic, tolerized T cells. Antisense IL-10 mediated activation of cytotoxic T cells provides a potent and specific therapeutic effect. Additionally, this treatment method is long lived because the immune system is able to replenish antigen-specific T cell clones once the precursor population is activated from the T cell repertoire.

An advantage of the invention is that immunology in general and T-cell mediated immunity have been studied for years, and much is known about properties of the complex system as a whole. A variety of pharmaceutical compositions have been suggested as immunomodulators that can enhance cellular immune responses such as those described by Kornbluth and Stone (Kornbluth and Stone 2006). The applicants' novel finding that functional IL-10 expression can be specifically downregulated provides a unique opportunity to harness this potent pathway to promote immune activation and prevention of any number of acute or chronic diseases. Given the fundamental importance of IL-10 in dampening the immune response and in the generation and maintenance of T-cell anergy, it is highly likely that the development of specific agents that ablate this immunosuppressive pathway will provide an important new therapeutic tool for the treatment of chronic or persistent diseases. It is envisioned that agents targeting IL-10, either used alone or in combination with other immunotherapeutic agents, will help achieve the elusive goal of reversing the T-cell anergy observed in many chronic or persistent diseases. This will have a great impact on the prevention and treatment of chronic or persistent diseases such as infections by HIV, HCV, HBV, *Chlamydia*, tuberculosis, CMV and EBV, among others. Moreover, such agents are likely to help make improved vaccines against infectious agents and therapeutic vaccines against the chronic or persistent infections such as those listed above and against chronic malignancies.

EXAMPLES

The following examples are presented to further illustrate and explain the present invention and should not be taken as limiting in any regard. The examples provide evidence that treatment with particular IL-10 splice altering peptide conjugated PMO (PPMO) will generate splice-altered IL-10 mRNA isoform expression in activated human monocyte-derived dendritic cells (MDDC).

A model has been established whereby mice treated with IL-10 splice altering PPMO were protected from lethal filovirus challenge. The reduction of IL-10 expression improves survival in mice infected with Zaire Ebola virus (ZEBOV). Furthermore, this protection is associated with a decrease in several inflammatory cytokines, as well as a small decrease in viral titers. Furthermore, IFN-$\alpha^{-/-}$ and T-bet$^{-/-}$ knockout mice succumb more quickly to ZEBOV infection than wildtype controls. Together, this data suggests that the Th1/Th2 axis plays a role in survival to ZEBOV infection, and IL-10-induced skewing to a Th2 response is detrimental. However, a decrease in inflammatory cytokines in a Th1 setting is also associated with survival, perhaps because too strong of an inflammatory response can lead to shock and immune suppression, suggesting that a balanced Th1 response is optimal for controlling ZEBOV infection.

IL-10 is an anti-inflammatory cytokine produced by DCs, monocytes-macrophages, B cells and various subsets of CD4+ and CD8+ T cells. The influence of IL-10 on Th1 responses in chronic viral infections, inhibition of NK cell and macrophage activity as well as an ability to ameliorate immunopathology has been well established. However, a role for IL-10 in the pathology of an acute viral infection such as Ebola virus is unknown. The examples demonstrate that although counterintuitive to the known anti-inflammatory activity of IL-10, inhibition of IL-10 expression and signaling by PPMO treatment leads to a marked reduction in mortality produced by a hemorrhagic virus challenge.

Materials and Methods

Monocyte-derived dendritic cells. Monocyte-derived DCs (MDDC) are prepared according the method by Romani et al (Romani, Gruner et al. 1994). Briefly, peripheral blood mononuclear cells (PBMC) are resuspended in 2% Human Serum (HS) medium and allowed to adhere to a T-75 (Costar) flask at 37 C for 1 h. After gentle rocking, nonadherent cells are removed and 10% HS medium containing 10 ng/ml of IL4 (Immunex) and 30 ng/ml of GM-CSF (Immunex) is added. After 5 days, cells (MDDC) are harvested with cell-dissociation medium (Sigma-Aldrich) and used as antigen presenting cells (APCs) in assays.

MDDC were either incubated with no morpholino, an irrelevant FITC-conjugated morpholino (3 uM), or with a morpholino targeted to the human IL-10 gene at exon 2 (3 uM) (P007-HuIL-10-SA2; SEQ ID NO:35 conjugated to SEQ ID NO:13). MDDC were unstimulated or stimulated overnight with LPS (100 ng/ml). RNA was isolated from 250,000 DC using the RNAeasy kit (Qiagen) and IL-10 cDNA products were identified by agarose gel electrophoresis following PCR amplification using a human IL10-specific primer set (HuIL10-fwd) 5'-CAACCTGCCTAACATGCTTC-3', HuIL10-rev 5'-TCTTCATTGTCATGTAGGCTTC-3'; SEQ ID NOs:31 and 32, respectively) for amplification of the region from exon 1 to exon 5. MDDC (20,000/well) were incubated with LPS (100 ng/ml) or zymosan (30 ug/ml) and placed in an IL-10 ELISPOT assay. IL-10 expression was assessed after an overnight incubation.

Murine bone marrow derived DCs (BMDCs) or T cells treated with the MuIL-10-SA2 PPMO (SEQ ID NO:36 conjugated to SEQ ID NO:18) resulted in the production of IL-10 mRNA with the exon 2 sequence excised as determined by PCR using a murine IL-10-specific primer set (MuIL0-fwd) 5'-GGAAGACAATMCTGCACCC-3', MuIL10-rev 5'-CAT-TCATGGCCTTGTAGACAC-3'; SEQ ID NOs:33 and 34, respectively) followed by gel electrophoresis and subsequent cloning and sequencing of gel isolated bands.

Animals. C57Bl/6 and BALB/c mice, aged 7-10 weeks of both sexes, were obtained from National Cancer Institute, Frederick Cancer Research and Development Center (Frederick, Md.). Mice were housed in microisolator cages and provided autoclaved water and chow ad libitum. C57Bl/6 and BALB/c mice were challenged by intraperitoneal injection with 1000 plaque-forming units (pfu) of mouse-adapted Ebola virus or Marburg virus, respectively, diluted in phosphate buffered saline (PBS) (Bray, Davis et al. 1998). Mice were treated with 50 micrograms of each of the anti-IL-10 PPMO (CPO6062-MuIL-10SA4; SEQ ID NO:40 conjugated to SEQ ID NO:17 or P007-MuIL-10SA4; SEQ ID NO:35 conjugated to SEQ ID NO:17) or an irrelevant control PPMO (CPO6062-GFP-globin; SEQ ID NO:40 conjugated to SEQ ID NO:30) split between two equivalent 50 microgram doses at 24 and 4 hours prior to Ebola or Marburg virus challenge. C57Bl/6 mice were challenged intraperitoneally with 1000 pfu of mouse-adapted Ebola virus (Bray, Davis et al. 1998). BALB/c mice were challenged with intraperitoneally with 1000 pfu of mouse-adapted Marburg virus.

Example 1

Anti-IL-10 PPMO Inhibit IL-10 Expression in Primary Human Dendritic Cells

Figure 2A:
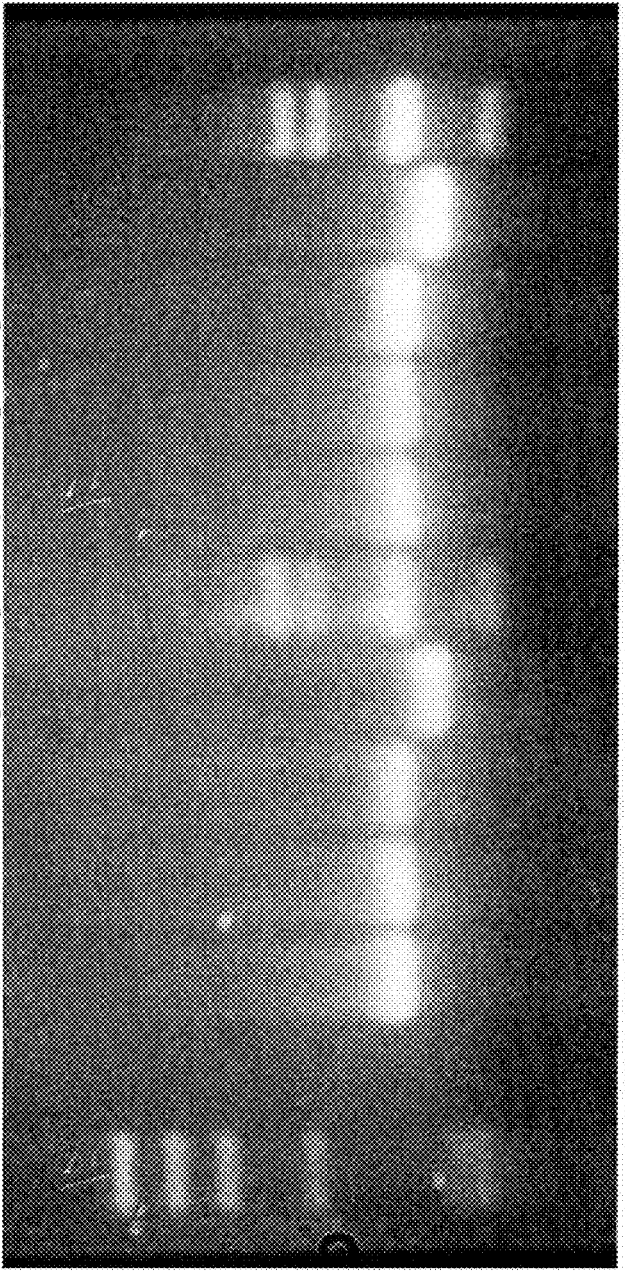
FIG. 2A shows that a PPMO targeted to exon 2 of the human IL-10 gene (SEQ ID NO:13 conjugated to SEQ ID NO:36) effectively alters IL-10 pre-mRNA processing by preventing the production of a full length mRNA transcript while untreated monocyte-derived dendritic cells (MDDC) treated with an irrelevant control PPMO did not alter the size of the IL-10 mRNA transcript.
Figure 2B:
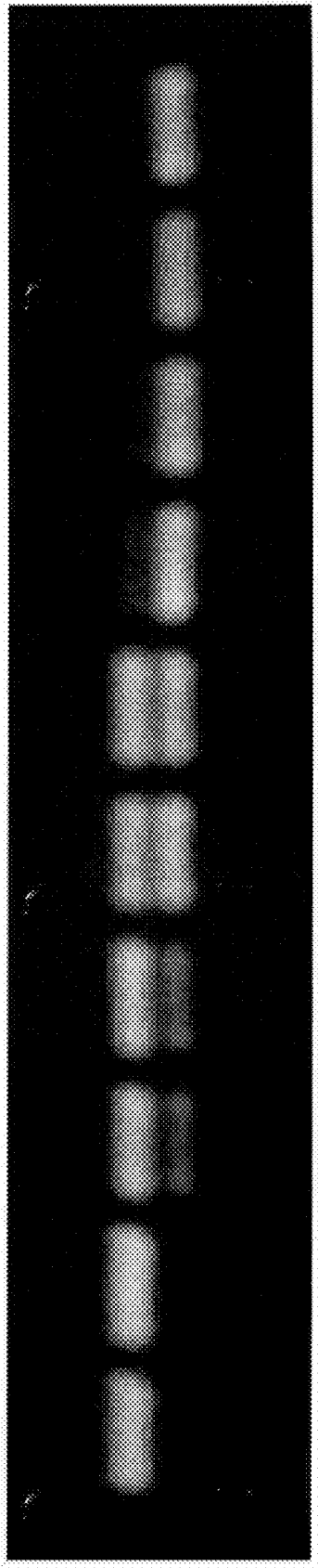
FIG. 2B shows that treatment of murine bone marrow derived dendritic cells with the MuIL-10-SA2 PPMO (SEQ ID NO:18 conjugated to SEQ ID NO:36) results in the production of IL-10 mRNA with exon 2 excised.

The ability of anti-IL-10 PPMO to target gene expression in both primary human monocyte-derived dendritic cells (MDDC) and T cells was determined. PPMO were tested for toxicity and uptake initially by trypan blue staining which showed that 98% of cells remained viable after an overnight incubation with the PPMO (3 uM) (P007-DSscr; SEQ ID NO:36 conjugated to SEQ ID NO:12). Uptake of an irrelevant PPMO (DSscr; SEQ ID NO:29) conjugated to a transport peptide (P007; SEQ ID NO:36) on the PMO 5'-terminus and conjugated to FITC on the PMO 3'-terminus, was assessed using flow cytometry after an 18-hour incubation using 0 (0% FITC+ cells), 3 uM (96% FITC+ cells), 1 uM (76% FITC+ cells), and 0.3 uM (24% FITC+ cells). MDDC were then treated with a series of PPMO targeting either the IL-10 AUG start codon (SEQ ID NO:12 conjugated to SEQ ID NO:36) or splice acceptor sites, isolated RNA (Qiagen RNAeasy kit) from the morpholino-treated cells and assessed by visualizing the gene-specific cDNA after reverse transcription of the isolated RNA. FIG. 2 shows that a PPMO targeted to exon 2 of the human IL-10 gene (P007-HuIL-10-SA2; SEQ ID NO:36 conjugated to SEQ ID NO:13), effectively blocked IL-10 gene transcription by preventing the production of an intact gene product while untreated MDDC or treatment with an irrelevant control PPMO (P007-DSscr; SEQ ID NO:36 conjugated to SEQ ID NO:29) did not alter the size of the IL-10 gene transcript. The smaller bands observed in lanes 5 and 10 were sequenced and confirmed the excision of Exon 2 from the IL-10 mRNA in cells exposed to these treatments. The larger bands observed in lanes 6 and 11 were also sequenced and shown to have been derived from mRNA with portions of Intron 2 included upstream of Exon 3.

Figure 3:
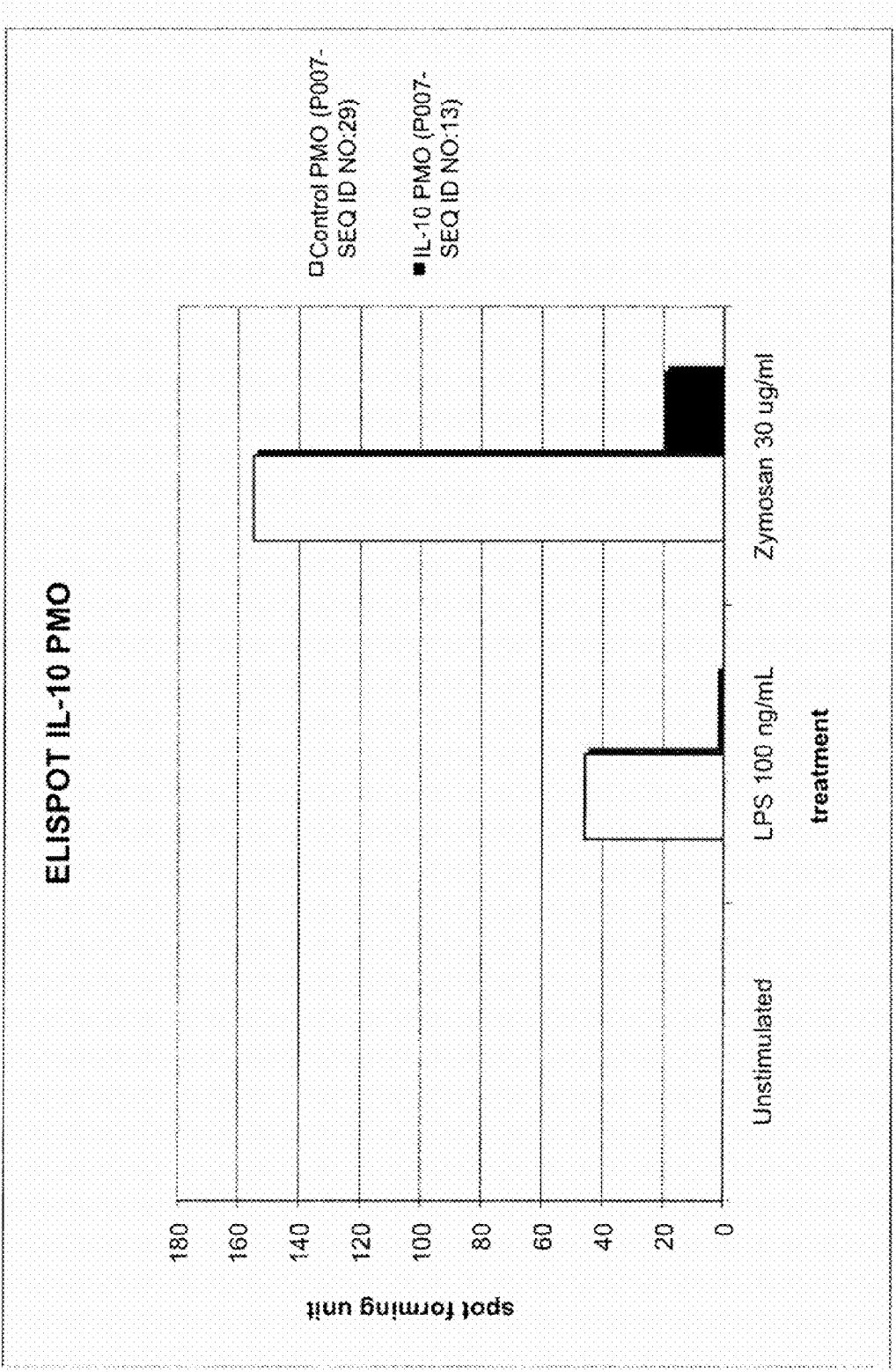
FIG. 3 shows a PPMO targeted to the human IL-10 gene (P007-HuIL-10-SA2; SEQ ID NO:36 conjugated to SEQ ID NO:13) functionally interferes with IL-10 production from primary human MDDC.

Functional inhibition of IL-10 production was also assessed using an ELISPOT assay. MDDC were incubated overnight with an anti-IL-10 PPMO (P007-HuIL-10-SA2; SEQ ID NO:36 conjugated to SEQ ID NO:13) at 3 uM. The ability the anti-IL-10 PPMO to functionally interfere with IL-10 expression was assessed after stimulation of the MDDC with the yeast cell wall component zymosan. FIG. 3 shows that untreated MDDC and MDDC treated with an irrelevant control morpholino produced similar amounts of IL-10 in sharp contrast to the anti-IL-10 PPMO-treated cells that were inhibited from producing IL-10.

Example 2

Activity of Anti-IL-10 PPMO Targeted to the IL-10 Exon 2 Splice Acceptor

The activity of the murine IL-10 SA2 PPMO (P007-MuIL-10-SA2; SEQ ID NO:36 conjugated to SEQ ID NO:18) was examined in vitro and in vivo to confirm IL-10 mRNA splicing and protein inhibition. Treatment of murine bone marrow derived DCs (BMDCs) or T cells with the MuIL-10-SA2 PPMO (SEQ ID NO:36 conjugated to SEQ ID NO:18) resulted in the production of IL-10 mRNA with the exon 2 sequence excised as determined by gel electrophoresis and subsequent cloning and sequencing of gel isolated bands. The splice altering activity was dose-dependent and sequence-specific (FIG. 2B) as was the production of IL-10 protein measured in the culture supernatants taken from treated BMDCs. In vivo splice-altering activity was confirmed by quantitative real-time PCR (qRT-PCR) with a FAM probe sequence specific for the unique sequence created by the joining of exon 1 to 3. B6 mice were injected intraperitoneally with 200 mg of IL-10 SA2 PPMO (SEQ ID NO:36 conjugated to SEQ ID NO:18) and treated with Zymosin for 2 hours. Splenocytes were harvested and mRNA isolated for RT-PCR detection. A qRT-PCR signal specific for the exon 1 to 3 junction was detected.

Example 3

Antiviral Efficacy of Anti-IL-10 PPMOs in Mice

To determine the in vivo efficacy of the anti-IL-10 PPMOs, the survival of mice (n=10 per experiment) treated with two 50 microgram doses of the PPMOs (CPO6062-MuIL-10SA4; SEQ ID NO:40 conjugated to SEQ ID NO:17 or P007-MuIL10SA4; SEQ ID NO:36 conjugated to SEQ ID NO:17) at 24 and 4 hours before challenge with 1000 plaque-forming units (pfu) of mouse-adapted Ebola virus was determined. Survival was compared to mice treated with two 50 microgram doses of either of two irrelevant PPMO (CPO6062-GFP-globin; SEQ ID NO:40 conjugated to SEQ ID NO:30 or a sequenced scrambled PMO (SEQ ID NO:29) also conjugated to CPO6062). The anti-IL-10 PPMOs exhibited potent prophylactic efficacy against lethal filovirus infection and provided nearly complete protection ((80-90% survival; FIG. 4) compared to the control PPMO (10-20% survival).

Additional components of the IL-10 signal transduction pathway (i.e., see FIG. 6) were determined to be critical for Ebola virus infection using the murine lethal challenge model. Dosing and timing protocols identical to that described above for anti-IL-10 PPMOs were used and two additional genes were identified as being essential for Ebola virus lethality. The murine IL-10 receptor alpha gene (IL10Ra) was targeted at the AUG start codon and the exon 2 and exon 6 splice acceptor sites using PPMO targeting sequences listed as SEQ ID NOs:19, and 21, respectively, conjugated to P007 (SEQ ID NO: 36). Similarly, the murine suppressor of cytokine signaling 3 (SOCS3) gene was targeted at the AUG start codon and exon 2 splice acceptor sites using PPMO targeting sequences listed as SEQ ID NOs:22 and 23, respectively, conjugated to P007 (SEQ ID NO: 36). The following table lists the gene target and the average percent survival of mice across multiple experiments (number of experiments shown as n=) and the maximum percent survival from any one experiment (10 mice used per experiment, except as noted). Data from experiments using PPMO targeting the IL-10 gene are listed for comparison.

TABLE 4

Protection from lethal Ebola virus challenge using PPMO that target IL-10 signaling

| Gene | PPMO | SEQ ID NO | Ave. Survival (n = # expts.) | Max. Survival |
|---|---|---|---|---|
| IL-10 | MuIL-10-SA4 | 17 | 59 (n = 3) | 100 |
| IL10Ra | MuIL10Ra-AUG | 19 | 33 (n = 3) | 60 |
| IL10Ra | MuIL10Ra-SA2 | 20 | 57 (n = 3) | 70 |
| IL10Ra | MuIL10Ra-SA6 | 21 | 43 (n = 3) | 80 |
| SOCS3 | MuSOCS3-AUG | 22 | 11* (n = 1) | 11* |
| SOCS3 | MuSOCS3-SA2 | 23 | 45 (n = 2) | 50 |

*Nine mice were used in this experiment with one survivor

Example 4

Anti-IL-10 PPMO Inhibition of IL-10 Expression in Human PBMC Stimulated with HIV-1 gp120

The gp120 envelope glycoprotein of HIV-1 is known to induce IL-10 expression in human monocytes and to induce anergy in human peripheral blood lymphocytes. These observations suggest that IL-10 plays an important role in the inhibitory effect of gp120 on PBMC proliferation and could contribute to the depressed immune responses associated with human immunodeficiency virus infection. To determine if the anti-IL-10 PPMO of the present invention are capable of inhibiting gp120-induced IL-10 expression, primary human PBMC were treated with recombinant HIV-1 gp120 and anti-IL-10 PPMO as described below.

Figure 5:
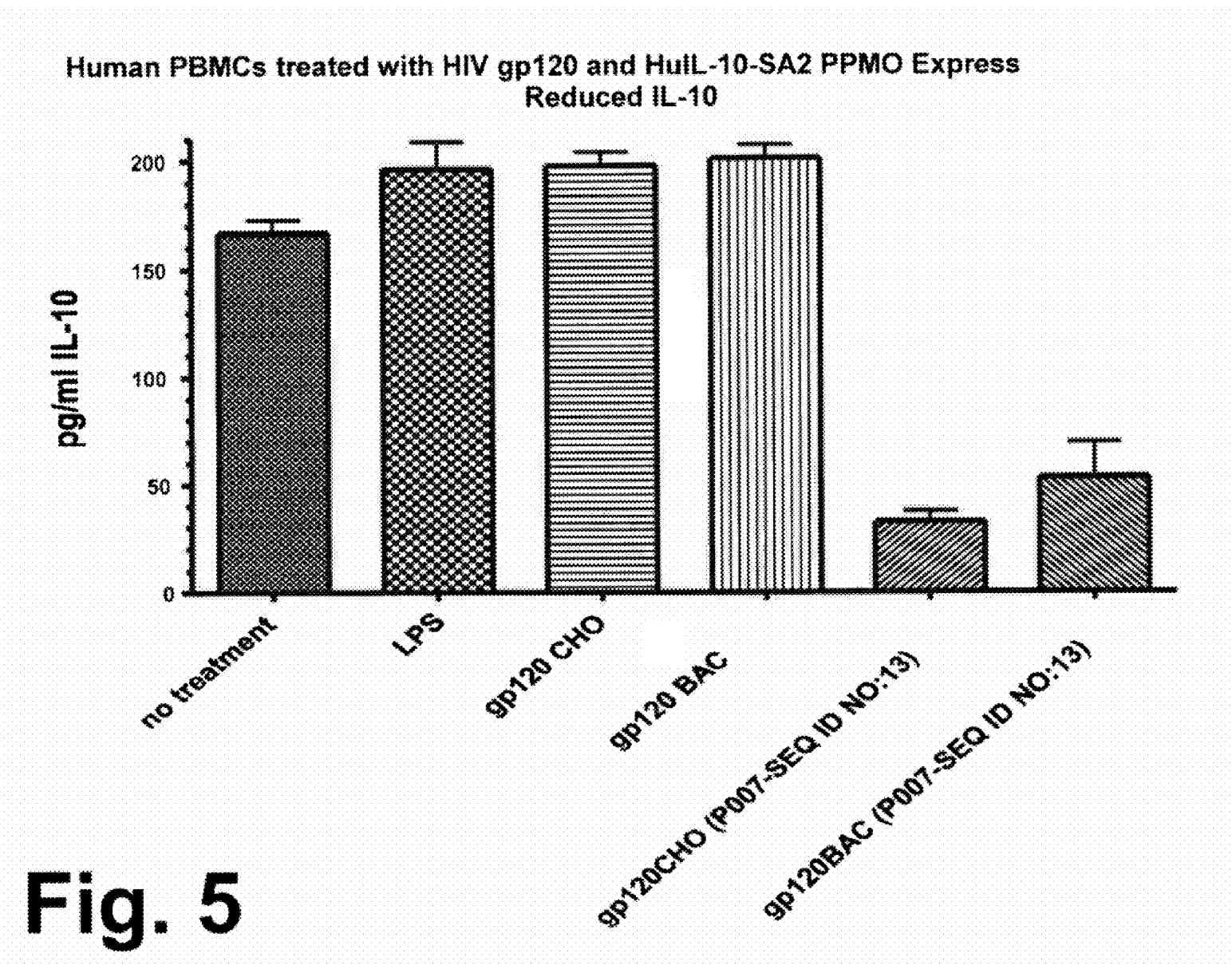

Human PBMCs from a single leukapheresis donor were plated at $2.5 \times 10^6$ cells/ml into the wells of a 24 well plate. Cells were left untreated or treated with LPS [0.1 ug/ml], Baculovirus derived recombinant HIV-1 gp120 [8 ug/ml] or Chinese hamster ovary cell-derived (CHO) recombinant HIV-1 gp120 [8 ug/ml]. One set of triplicate wells of each gp120 treatment received anti-IL-10 SA2 PPMO [5 µM] (P007-HuIL-10-SA2; SEQ ID NO:36 conjugated to SEQ ID NO:13) added directly to the cell culture media. The culture cells were incubated for 72 hrs after which the cells were dislodged by vigorous pipetting and transferred to microcentrifuge tubes. The supernatants were removed from the cells by centrifugation and then transferred to new tubes, both were immediately frozen on dry ice and then stored at −70 C. The content of IL-10 in the supernatants was quantified using a human IL-10 bead assay (Bender MedSystems, Vienna, Austria) and analyzed by flow cytometry using a FC-500 (Beckman Coulter) and FloCytomix Pro software (Bender MedSystems). FIG. 5 shows the level of IL-10 knock down in anti-IL-10 PPMO-treated PBMC as described. The inhibition of gp120-induced IL-10 expression was as much as 83% in the CHO gp120-treated PBMC.

Total cellular RNA was harvested from the treated PBMC pellets after thawing using a QiaSpin mRNA Isolation Kit (Qiagen). RT-PCR was performed using SuperScript III One-Step RT-PCR (Invitrogen), an iQcycler (BioRad) and the human IL-10 specific PCR primers described above. The expected exon2-deleted altered splice-form was detected using this assay.

SEQUENCE LISTING

| Name | Sequence (5' to 3') | Seq ID No. |
|---|---|---|
| Target Sequences | | |
| IL10 AUG | CAAGACAGACTTGCAAAAGAAGGATGCACAGCTCAGCACTGCTCTGTTG | 1 |
| IL10 Exon 2 | CAAATGAAGGATCAGCTGGACAACT | 2 |
| IL10 Exon 2SA | CATTCTCCTTTTGTTCTTCCTGCAG/CAAATGAAGGATCAGCTGGACAACT | 3 |
| IL10 Exon 3SA | ACTCACCTTTGGCTCCTGCCCTTAG/GGTTACCTGGGTTGCCAAGCCTTGT | 4 |
| IL10 Exon 4 | CATCGATTTCTTCCCTGTGAAAACA | 5 |
| Exon 2 to Exon 4 of preprocessed human IL-10 | TCATTCTCCTTTTGTTCTTCCTGCAGCAAATGAAGGATCAGCTGGACAACTT GTTGTTAAAGGAGTCCTTGCTGGAGGACTTTAAGGTGAGAGCAGGGGCGGGG TGCTGGGGGAGTGTGCAGCATGATTAAGGGAAGGGAGACTCTGCTTCCTGAT TGCAGGGAATTGGGTTTGTTTCCTTCGCTTTGAAAAGGAGAAGTGGGAAGAT GTTAACTCAGCACATCCAGCAGCCAGAGGGTTTACAAAGGGCTCAGTCCCTT CGGGGAGGCTTCTGGTGAAGGAGGATCGCTAGAACCAAGCTGTCCTCTTAAG CTAGTTGCAGCAGCCCCTCCTCCCAGCCACCTCCGCCAATCTCTCACTCACC TTTGGCTCCTGCCCTTAGGGTTACCTGGGTTGCCAAGCCTTGTCTGAGATGA TCCAGTTTTACCTGGAGGAGGTGATGCCCCAAGCTGAGAACCAAGACCCAGA CATCAAGGCGCATGTGAACTCCCTGGGGGAGAACCTGAAGACCCTCAGGCTG AGGCTACGGCGCTGTGTAAGTAGCAGATCAGTTTTTTCCCTTGCAGCTGCCC CCAAAATACCATCTCCTACAGACCAGCAGGGACACTCACATCCACAGACACA GCAAAGACACAGACTGGCAGAGCTAGCTGTAAATGAGGAAAGACTCCTGGAG TCAGATCTCTTGCTCATTTCTCTTTGAGCAGGCGTTGGGGGTGGCTGCTAGG CATTTACATGTGAAATTTGCAAACAGCTTTCCTGTTATTTGTGAGTCATTTG TGGGTTATTAACTACTCCCCTCTCTCTTCATAAAAGGAGCCCAGAGCTTCAG TCAGGCCTCCACTGCCTCTTTGTAACTAGACCCTGGGCGGGGAGCTAAGGTT CCCAAGCAGAGGAAACATCATTCACCTCTTTTAATCTCAATGTTTTGAAAGC AAAGCTCTAAGAAGGGCCCAATTGACTGACAGGATTTCCCCTGGCATTTTAG AAGGGACAAGGGGGCTATTCATCCCCAGGCTAGTGTCTATGAGTAATTCCTC CAGGTAATTTATTTCTCCAACTGAAATGATGCCCTCACTACTAATGGTTTCC CCTGTTCTGTCACCAATATTGGAAAATCAGTTGGTGTCTATTTGTAGGACAA GGCTATGTGAAGGGTTTGGTCCCAGTAGCTTCCCTCCTCAGATGCTTAGAAG TGTTCCTCGGTGGCTGTGACTGACGGGGAGGAACAGGAGAGAGGAGGCAGAAA AGGACAGCCTGAAGAATGCCTCGCTCAGCACTGCAGGAGATACTGTAGAGTT CTGGGGGAGGAAGGAATCCCAAGACCTGGCTTGTCATCCAAGCCTTGCAAAC ATCTTGGAGTGAGTCCTGGAGAAATACATTTAACTCCCAGGGCCATGGAAGC AGGGCTCAGTTCTCTCTGGGAGCTGTGAGGCAAGGCATTTGGATAAATCTGG CCTCCTCATGATGCCACCAGCTTGrCCCCTAAGTGTGATGGACATGGAGCTG GAAGCCAGGATCACCAACACTTTCTCTTTTCTTCCACAGCATCGATTTCTTC CCTGTGAAAACAAGAGCAAGGCCGTGGAGCAGGTGAAGAATGCCTTTAATAAG | 6 |
| SOCS3 AUG | CAGATCCACGCTGGCTCCGT<u>GCGCC</u>ATGGTCACCCACAGCAAGTTTCCCG | 7 |
| SOCS3 Exon 2SA | CGCGCTCGCGCCTTCCTCTCCGCAG | 8 |
| IL10Ra AUG | CCCCGGACGATGCGGCGCGCC<u>CAGG</u>ATGCTGCCGTGCCTCGTAGTGCTGC | 9 |
| IL10Ra Exon 2SA | GTGGTACTGACACTCTTCTCCCCAG | 10 |
| IL10Ra Exon 6SA | CAAACACATCTCTCTGGGCCTGCAG | 11 |
| Targeting Sequences | | |
| HuIL-10-AUG | CAGTGCTGAGCTGTGCATGCC | 12 |
| HuIL-10-SA2 | GTCCAGCTGATCCTTCATTTG | 13 |
| HuIL-10-SA3 | TCATCTCAGACAAGGCTTGGC | 14 |
| HuIL-10-SD2 | CTTAAAGTCCTCCAGCAAGGAC | 15 |
| HuIL-10-SA4 | TTTCACAGGGAAGAAATCGATG | 16 |
| MuIL-10-SA4 | GGAGAAATCGATGCTGAAGAA | 17 |
| MuIL-10-SA2 | GTCCAGCTGGTCCTTTGTGTT | 18 |
| MuIL10Ra-AUG | GCAAACGCGACAACATCCTG | 19 |
| MuIL10Ra-SA2 | AAGGGCTTGGCAGTTCTGTCC | 20 |

-continued

SEQUENCE LISTING

| Name | Sequence (5' to 3') | Seq ID No. |
|---|---|---|
| MuIL10Ra-SA6 | TCAGGTTGGTCACAGTGAAAT | 21 |
| MuSOCS3-AUG | TTGCTGTGGGTGACCATGGCG | 22 |
| MuSOCS3-SA2 | GCCGCTACCGCATCCCGGGGA | 23 |
| HuIL10Ra-AUG | CTACGAGGCACGGCAGCATCCTG | 24 |
| HuIL10Ra-SA2 | CGGAGGGCTGGGCAGCTCTGTCC | 25 |
| HuIL10Ra-SA6 | GATGACGTTGGTCACGGTGAAAT | 26 |
| HuSOCS3-AUG | CTTGCTGTGGGTGACCATGGCGC | 27 |
| HuSOCS3-SA2 | GCCGCTACCGCATCCCGGGGGG | 28 |
| DSscr | AGTCTCGACTTGCTACCTCA | 29 |
| GFP-globin | TGCTATTACCTTAACCCAGA | 30 |
| HuIL10-fwd | CAACCTGCCTAACATGCTTC | 31 |
| HuIL10-rev | TCTTCATTGTCATGTAGGCTTC | 32 |
| MuIL10-fwd | GGAAGACAATAACTGCACCC | 33 |
| MuIL10-rev | CATTCATGGCCTTGTAGACAC | 34 |
| Peptide Transporters | | |
| (RRAhx)$_4$B | RRAhxRRAhxRRAhxRRAhXB | 35 |
| P007 | RAhxRRAhxRRAhxRRAhxRAhxB | 36 |
| (AhxRR)$_4$AhxB | AhxRRAhxRRAhxRRAhxRRAhxB | 37 |
| (RAhx)$_6$B | RAhxRAhxRAhxRAhxRAhxRAhxB | 38 |
| (RAhx)$_8$B | RAhxRAhxRAhxRAhxRAhxRAhxRAhxB | 39 |
| (RAhxR)$_3$AhxB | RAhxRRAhXRRAhXR AhxB | 40 |
| CPO6062 | RAhxRRBRRAhxRRBRAhxB | 41 |
| ((RB)$_3$RAhx)$_2$B | RBRBRBRAhxRBRBRBRAhxB | 42 |

It is claimed:

1. A method of treating a mammalian subject infected with a pathogen which acts to up-regulate IL-10 during infection in a mammalian host, as evidenced by increased serum levels of IL-10, comprising administering to the subject, a therapeutically effective amount of an antisense composition containing an antisense oligonucleotide compound (i) composed of morpholino subunits and phosphorus-containing intersubunit linkages joining a morpholino nitrogen of one subunit to a 5' exocyclic carbon of an adjacent subunit, (ii) capable of uptake by monocytes, lymphocytes, and dendritic cells in a mammalian subject, (iii) containing between 10-40 nucleotide bases, and (iv) having a targeting sequence complementary to at least 12 contiguous bases of the 5'-most 25 bases of exon 2 or exon 4 of the preprocessed human IL-10 transcript contained within SEQ ID NO:6, and identified by SEQ ID NOS:2 and 5, respectively.

2. The method of claim 1, wherein the targeting sequence is complementary to at least 12 contiguous bases of SEQ ID NO:5 in SEQ ID NO:6.

3. The method of claim 1, wherein the targeting sequence is complementary to at least 12 contiguous bases of SEQ ID NO:2 in SEQ ID NO:6.

4. The method of claim 1, wherein the target sequence is contained entirely within SEQ ID NOS:2 or 5.

5. The method of claim 1, wherein the composition administered contains a second oligonucleotide antisense compound having a targeting sequence complementary to at least 12 contiguous bases of another splice-site target sequence of the preprocessed human IL-10 transcript contained within SEQ ID NO:6.

6. The method of claim 1, wherein the antisense oligonucleotide compound which is administered is conjugated to an arginine-rich polypeptide effective to promote uptake of the compound into monocytes, lymphocytes, and dendritic cells.

7. The method of claim 1 for use in treating a mammalian subject infected with a viral pathogen, which further includes administering to the subject, an anti-viral compound effective to inhibit replication of the viral pathogen in the mammalian host.

8. The method of claim 1 for use in treating a mammalian subject infected with a bacterial pathogen, which further includes administering to the subject, an anti-bacterial compound effective to inhibit replication of the bacterial pathogen in the mammalian host.

9. A pharmaceutical composition for treatment of a pathogen which acts to up-regulate IL-10 during infection in a mammalian host, as evidenced by increased serum levels of IL-10, comprising (a) a pathogen antigenic component capable of eliciting an immune response against the pathogen, (b) an antisense oligonucleotide compound (i) composed of morpholino subunits and phosphorus-containing intersubunit linkages joining a morpholino nitrogen of one subunit to a 5' exocyclic carbon of an adjacent subunit, (ii) capable of uptake by monocytes, lymphocytes, and dendritic cells in a mammalian subject, (iii) containing between 10-40 nucleotide bases, and (iv) having a targeting sequence complementary to at least 12 contiguous bases of the 5'-most 25 bases of exon 2 or exon 4 of the preprocessed human IL-10 transcript contained within SEQ ID NO:6, and identified by SEQ ID NOS:2 and 5, respectively, and (c) an adjuvant in which the antigenic component and antisense compound are formulated.

10. The composition of claim 9, which further includes a second antisense oligonucleotide compound having a targeting sequence complementary to at least 12 contiguous bases of another splice-site target sequence of the preprocessed human IL-10 transcript contained within SEQ ID NO:6.

11. The composition of claim 9, wherein the antisense oligonucleotide compound is conjugated to an arginine-rich polypeptide effective to promote uptake of the compound into monocytes, lymphocytes, and dendritic cells.

12. The composition of claim 9, wherein the arginine-rich polypeptide has the sequence defined by SEQ ID NO:36 or SEQ ID NO:40.

13. The composition of claim 9, wherein the intersubunit linkages linking the morpholino subunits are phosphorodiamidate linkages having the structure:

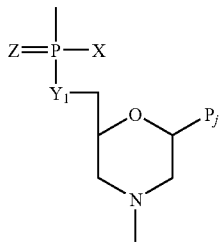

where $Y_1=O$, $Z=O$, Pj is a purine or pyrimidine base-pairing moiety effective to bind, by base-specific hydrogen bonding, to a base in a polynucleotide, and X is alkyl, alkoxy, thioalkoxy, or alkyl amino, including wherein $X=NR_2$, where each R is independently hydrogen or methyl.

14. An antisense oligonucleotide compound (i) composed of morpholino subunits and phosphorus-containing intersubunit linkages joining a morpholino nitrogen of one subunit to a 5' exocyclic carbon of an adjacent subunit, (ii) capable of uptake by monocytes, lymphocytes, and dendritic cells in a mammalian subject, (iii) containing between 10-40 nucleotide bases, and (iv) having a targeting sequence complementary to at least 12 contiguous bases of a target sequence composed of 5'-end 25 bases of exon 2 or exon 4 of the preprocessed human IL-10 transcript contained within SEQ ID NO:6, and identified by SEQ ID NOS:2 and 5, respectively.

15. The compound of claim 14, wherein the targeting sequence is complementary to at least 12 contiguous bases of SEQ ID NO:5 in SEQ ID NO:6.

16. The compound of claim 14, wherein the targeting sequence is complementary to at least 12 contiguous bases of SEQ ID NO:2 in SEQ ID NO:6.

17. The compound of claim 14, wherein the target sequence is contained entirely within SEQ ID NOS:2 or 5.

18. The compound of claim 14, which is conjugated to an arginine-rich polypeptide effective to promote uptake of the compound into monocytes, lymphocytes, and dendritic cells.

19. The compound of claim 18, wherein the arginine-rich polypeptide has the sequence defined by SEQ ID NO:36 or SEQ ID NO:40.

20. The compound of claim 14, wherein the intersubunit linkages linking the morpholino subunits are phosphorodiamidate linkages having the structure:

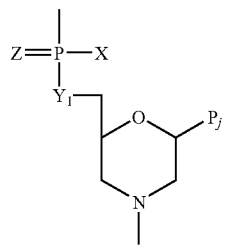

where $Y_1=O$, $Z=O$, Pj is a purine or pyrimidine base-pairing moiety effective to bind, by base-specific hydrogen bonding, to a base in a polynucleotide, and X is alkyl, alkoxy, thioalkoxy, or alkyl amino, including wherein $X=NR_2$, where each R is independently hydrogen or methyl.

21. The compound of claim 20, wherein the intersubunit linkages are uncharged linkages interspersed with piperazine-containing linkages, where the total number of piperazine-containing linkages is between 2 and no more than half of the total number of linkages.

22. The compound of claim 21, wherein the piperazine-containing linkages have the structure X is 1-piperazinyl.

* * * * *